(12) United States Patent
Kim et al.

(10) Patent No.: US 9,023,489 B2
(45) Date of Patent: May 5, 2015

(54) RED PHOSPHORESCENT COMPOUNDS AND ORGANIC ELECTROLUMINESCENT DEVICES USING THE SAME

(75) Inventors: Jung Keun Kim, Seoul (KR); Jeong Dae Seo, Incheon (KR); Hyun Cheol Jeong, Jinju-si (KR); Chun Gun Park, Seoul (KR); Jong Kwan Bin, Yongin (KR); Kyung Hoon Lee, Seoul (KR); Sung Hoon Pieh, Seoul (KR)

(73) Assignee: LG Display Co., Ltd., Seoul (KR)

( * ) Notice: Subject to any disclaimer, the term of this patent is extended or adjusted under 35 U.S.C. 154(b) by 881 days.

(21) Appl. No.: 11/593,148

(22) Filed: Nov. 6, 2006

(65) Prior Publication Data
US 2007/0104980 A1 May 10, 2007

(30) Foreign Application Priority Data

| | | |
|---|---|---|
| Nov. 7, 2005 | (KR) | 10-2005-0105978 |
| Nov. 7, 2005 | (KR) | 10-2005-0105979 |
| Nov. 7, 2005 | (KR) | 10-2005-0105982 |
| Mar. 23, 2006 | (KR) | 10-2006-0026629 |

(51) Int. Cl.
| | |
|---|---|
| H01L 51/54 | (2006.01) |
| C09K 11/06 | (2006.01) |
| C07F 15/00 | (2006.01) |
| H01L 51/00 | (2006.01) |
| H01L 51/50 | (2006.01) |

(52) U.S. Cl.
CPC ........ C07F 15/0033 (2013.01); H01L 51/0085 (2013.01); H01L 51/5016 (2013.01); C09K 11/06 (2013.01); C09K 2211/1029 (2013.01); C09K 2211/185 (2013.01); Y10S 428/917 (2013.01)

(58) Field of Classification Search
CPC ............ C07F 15/0033; H01L 51/0085; H01L 51/5016; C09K 11/06; C09K 2211/1029; C09K 2211/185
See application file for complete search history.

(56) References Cited

U.S. PATENT DOCUMENTS

| | | | |
|---|---|---|---|
| 6,835,469 B2 | 12/2004 | Kwong et al. | |
| 2003/0068526 A1 | 4/2003 | Kamatani et al. | |
| 2003/0072964 A1* | 4/2003 | Kwong et al. | 428/690 |
| 2003/0218418 A9 | 11/2003 | Sato et al. | |
| 2004/0127710 A1 | 7/2004 | Park et al. | 546/2 |
| 2007/0128468 A1 | 6/2007 | Kim et al. | |

FOREIGN PATENT DOCUMENTS

| | | |
|---|---|---|
| CN | 1582073 | 2/2005 |
| KR | 10-2005-0037479 | 4/2005 |
| WO | WO 02/44189 | 6/2002 |
| WO | WO 03/040256 | 5/2003 |
| WO | WO 2006/014599 | 2/2006 |

OTHER PUBLICATIONS

Fang, Kai-Hung, et al., Color Tuning of Iridium Complexes—Part I : Substituted Phenylisoquinoline-Based Iridium Complexes as the Triplet Emitter,: Inorganica Chimica Acta, vol. 359, No. 2, Jan. 20, 2006, pp. 441-450, (XP005232525).

Huang, Yu-Ting, et al., "Bi-Substituted Effect on Phenylisiquinoline Iridium (III) Complexes," The American Chemical Society, Organometallics, vol. 24, No. 25, Nov. 5, 2005, pp. 6230-6238, (XP009079764).

Lee, Young Hee, et al., "Theoretical Study of Ir(III) Complexes of Fluorinated Phenylbenzoquinoline as Red Phosphorescent Material," The Japan Society of Applied Physics, Japanese Journal of Applied Physics, vol. 45, No. 1B, Published Online Jan. 20, 2006, pp. 563-567, (XP009079763).

(Continued)

*Primary Examiner* — Michael H Wilson
(74) *Attorney, Agent, or Firm* — Morgan, Lewis & Bockius LLP

(57) ABSTRACT

Disclosed herein are red phosphorescent compounds of the following formula:

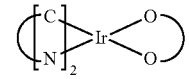

wherein

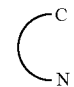

includes a phenyl part and a quinoline part, each ring of the phenyl part having at least one substituent selected from hydrogen, $C_1$-$C_4$ alkyl groups and $C_1$-$C_4$ alkoxy groups
and

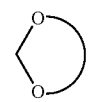

is selected from 2,4-pentanedione, 2,2,6,6,-tetramethyl-heptane-3,5-dione, 1,3-propanedione, 1,3-butanedione, 3,5-heptanedione, 1,1,1-trifluoro-2,4-pentanedione, 1,1,1,5,5,5-hexafluoro-2,4-pentanedione and 2,2-dimethyl-3,5-hexanedione.

4 Claims, 2 Drawing Sheets

(56) References Cited

OTHER PUBLICATIONS

Li, Chien-Le et al., "Yellow and Red Electrophosphors Based on Linkage Isomers of Phenylisoquinolinyliridium Complexes: Distinct Differences in Photophysical and Electroluminescence Properties," Advanced Function Materials, vol. 15, No. 3, Mar. 2005, pp. 387-395, (XP001224595).

Yang, Cheng-Hsien et la., "Color Tuning or Iridium Complexes FPR Organic Lignt-Emitting Diodes: The Electronegative Effect and π-Conjunction Effect," Journal of Organometallic Chemistry, vol. 691, No. 12, Jun. 1, 2006, pp. 2767-2773, (XP005429595).

Yang, Cheng-Hsien, et al., "Synthesis of a High-Efficiency Red Phosphorescent Emitter for Organic Lignt-Emitting Diodes," Journal of Materials Chemistry, vol. 14, No. 6, Feb. 11, 2004, pp. 947-950, (XP009079766).

European Office Action dated Apr. 4, 2007.

* cited by examiner

CuPC

NPD (btp)$_2$Ir(acac)

BAlq

Alq$_3$

CBP

RED PHOSPHORESCENT COMPOUNDS AND ORGANIC ELECTROLUMINESCENT DEVICES USING THE SAME

This application claims the benefit of Korean Patent Application No. 10-2005-0105978 filed on Nov. 7, 2005, No. 10-2005-0105979 filed on Nov. 7, 2005, No. 10-2005-0105982 filed on Nov. 7, 2005 and No. 10-2006-0026629 filed on Mar. 23, 2006 which are hereby incorporated by reference as if fully set forth herein.

BACKGROUND OF THE INVENTION

1. Field of the Invention

The present invention relates to red light-emitting phosphorescent compounds (hereinafter, referred to simply to as 'red phosphorescent compounds') and organic electroluminescent (EL) devices using the same. More particularly, the present invention relates to red phosphorescent compounds, and organic electroluminescent devices comprising a laminate of an anode, a light-emitting layer and a cathode wherein one of the red phosphorescent compounds is used as a dopant of the light-emitting layer.

2. Discussion of the Related Art

With recent trends toward large-area displays, there has been increased demand for flat display devices that take up little space. In particular, technology of organic electroluminescent (EL) devices (also termed 'organic light emitting diodes (OLEDs)') as flat display devices has been rapidly developed. A variety of prototypes of organic electroluminescent (EL) devices have been reported to date.

When charge carriers are injected into an organic film formed between an electron injecting electrode (cathode) and a hole injecting electrode (anode) of an organic electroluminescent device, electrons combine with holes to create electron-hole pairs, which then decay to emit light. Organic electroluminescent devices have advantages in that they can be fabricated on flexible transparent substrates (e.g., plastic substrates) and can be operated at a voltage (e.g., 10V or below) lower than voltages required to operate plasma display panels (PDPs) and inorganic electroluminescent devices. Other advantages of organic electroluminescent devices are relatively low power consumption and excellent color representation. Further, since organic electroluminescent (EL) devices can emit light of three colors (i.e., green, blue and red), they have been the focus of intense interest lately as next-generation display devices capable of producing images of various colors. A general method for fabricating organic EL devices will be briefly explained below.

(1) First, a transparent substrate is covered with an anode material. Indium tin oxide (ITO) is generally used as the anode material.

(2) A hole injecting layer (HIL) is formed to a thickness of 10 to 30 nm on the anode. Copper (II) phthalocyanine (CuPc) is mainly used as a material of the hole injecting layer.

(3) A hole transport layer (HTL) is introduced into the resulting structure. The hole transport layer is formed by depositing 4,4'-bis[N-(1-naphthyl)-N-phenylamino]-biphenyl (NPB) to a thickness of about 30 to about 60 nm on the hole injecting layer.

(4) An organic light-emitting layer is formed on the hole transport layer. If necessary, a dopant may be added to a material for the organic light-emitting layer. For green light emission, tris(8-hydroxyquinoline)aluminum ($Alq_3$) as a material for the organic light-emitting layer is deposited to a thickness of about 30 to about 60 nm on the hole transport layer, and N-methylquinacridone (MQD) is mainly used as the dopant.

(5) An electron transport layer (ETL) and an electron injecting layer (EIL) are sequentially formed on the organic light-emitting layer. Alternatively, an electron injecting/transport layer is formed on the organic light-emitting layer. In the case of green light emission, since $Alq_3$ has excellent electron-transport ability, the formation of the electron injecting/transport layer may be unnecessary.

(6) A cathode material is coated on the electron injecting layer, and finally a passivation film is covered thereon.

The type of the organic electroluminescent devices (i.e. blue, green and red light-emitting devices) will be determined depending on the kind of materials for the light-emitting layer.

In the light-emitting layer, holes injected from the anode are recombined with electrons injected from the cathode to form excitons. Singlet excitons and triplet excitons are involved in the fluorescence and phosphorescence processes, respectively. Fluorescent materials using triplet excitons, which are involved in the phosphorescence process, whose probability of formation is 75%, exhibit high luminescence efficiency, as compared to fluorescent materials using singlet excitons whose probability of formation is 25%. In particular, the luminescence efficiency of red phosphorescent materials is considerably high, compared to that of fluorescent materials. Accordingly, a number of studies associated with the use of red phosphorescent materials in organic electroluminescent devices are being made to enhance the luminescence efficiency of the organic electroluminescent devices.

Phosphorescent materials for use in organic EL devices must satisfy the requirements of high luminescence efficiency, high color purity and long luminescence lifetime. As shown in FIG. 1, as the color purity of an organic EL device using a red phosphorescent material becomes higher (i.e. as the x-values on CIE chromaticity coordinates increase), the spectral luminous efficacy of the organic EL device decreases, making it difficult to achieve high luminescence efficiency of the organic EL device.

Thus, there is a demand to develop a red phosphorescent compound that exhibit desirable chromaticity coordinate characteristics (CIE color purity $X \geq 0.65$), high luminescence efficiency, and long luminescence lifetime.

SUMMARY OF THE INVENTION

Accordingly, the present invention is directed to red phosphorescent compounds and organic electroluminescent (EL) devices using the same that substantially obviate one or more problems due to limitations and disadvantages of the related art.

An object of the present invention is to provide compounds of Formulas 1 to 4 that follow.

Another object of the present invention is to provide organic electroluminescent (EL) devices with high color purity, high luminance and long lifetime which use one of the compounds as a dopant of a light-emitting layer.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, there is provided a red phosphorescent compound of Formula 1:

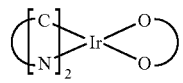 (1)

wherein

is

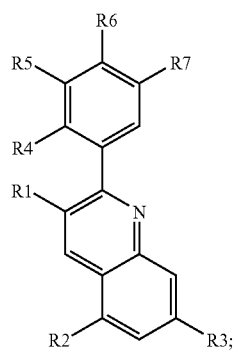

R1, R2 and R3 are independently a $C_1$-$C_4$ alkyl group; R4, R5, R6 and R7 are independently selected from hydrogen, $C_1$-$C_4$ alkyl groups and $C_1$-$C_4$ alkoxy groups; and

is selected from 2,4-pentanedione

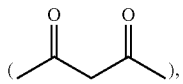

2,2,6,6,-tetramethylheptane-3,5-dione

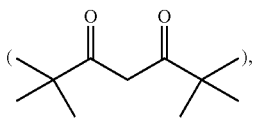

1,3-propanedione

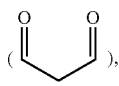

1,3-butanedione

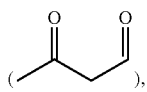

3,5-heptanedione

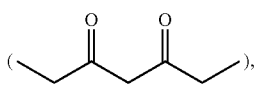

1,1,1-trifluoro-2,4-pentanedione

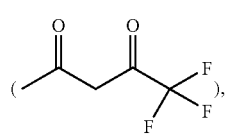

1,1,1,5,5,5-hexafluoro-2,4-pentanedione

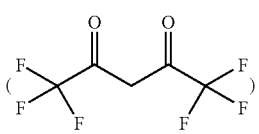 [SMILES: O=C(CC(=O)C(F)(F)F)C(F)(F)F]

and 2,2-dimethyl-3,5-hexanedione

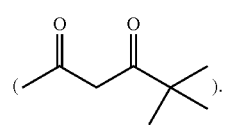

in Formula 1 is selected from the following compounds:

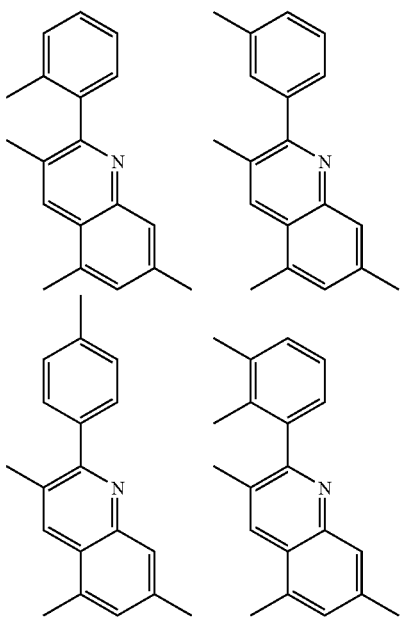

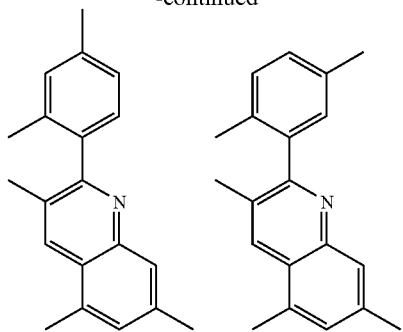
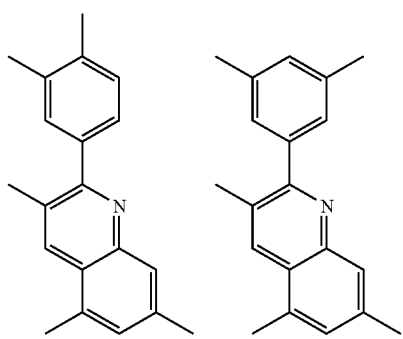
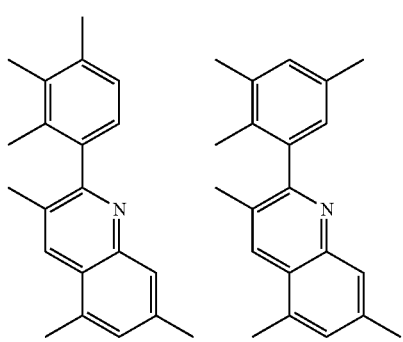
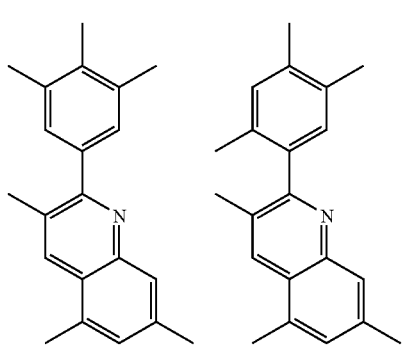
Examples of preferred compounds that can be represented by Formula 1 include the following compounds:
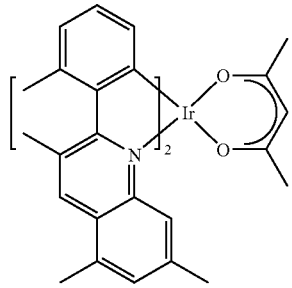
RD-1
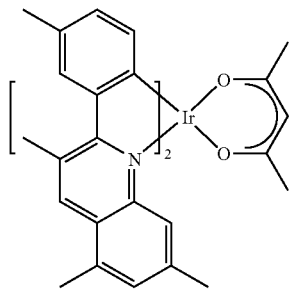
RD-2
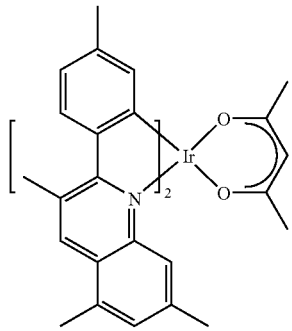
RD-3
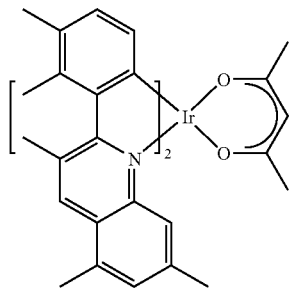
RD-4
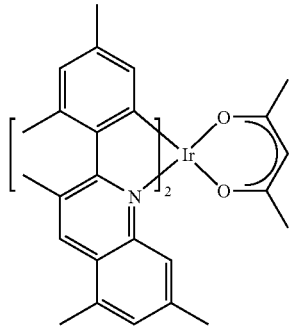
RD-5

RD-6
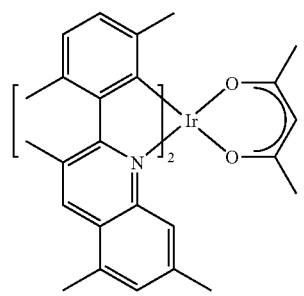
RD-11
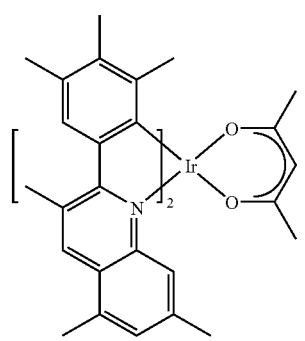
RD-7
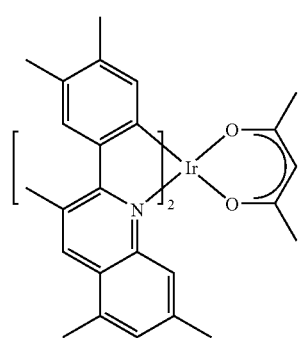
RD-12
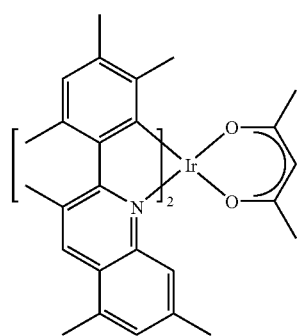
RD-8
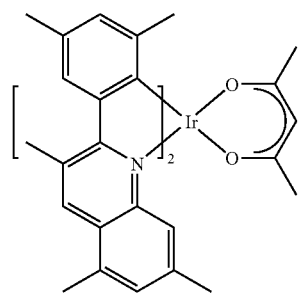
RD-13
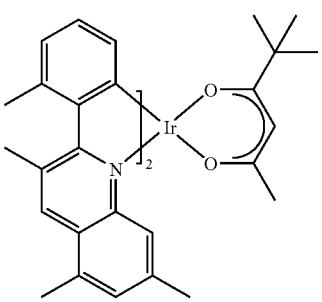
RD-9
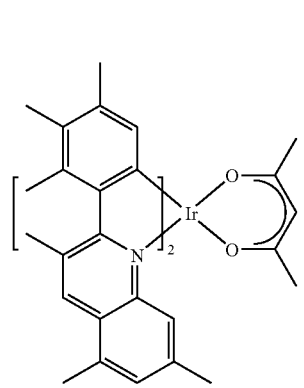
RD-14
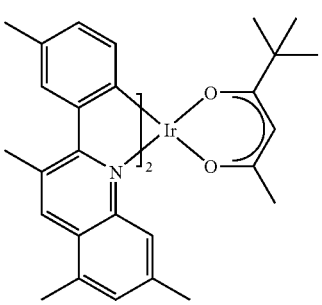
RD-10
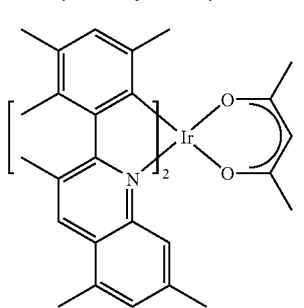
RD-15
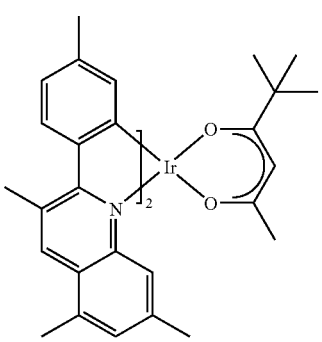

RD-16
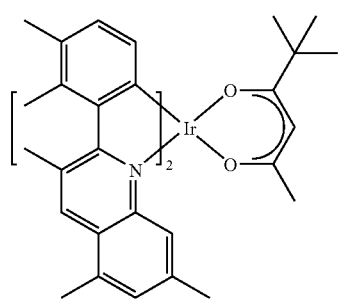
RD-17
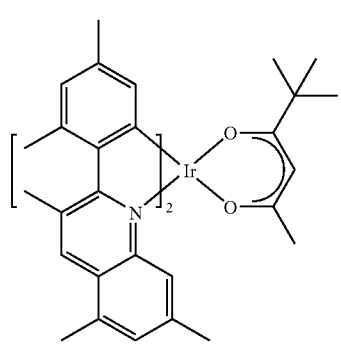
RD-18
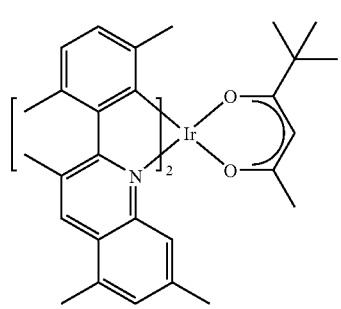
RD-19
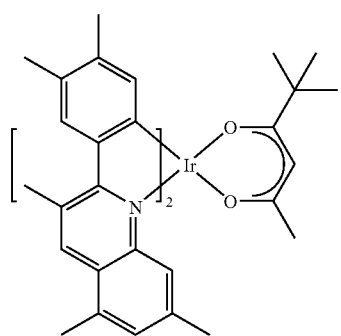
RD-20
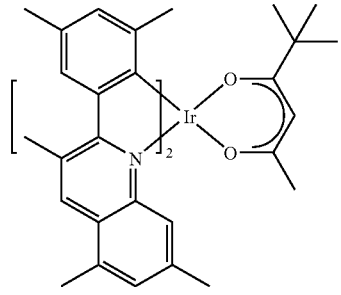
RD-21
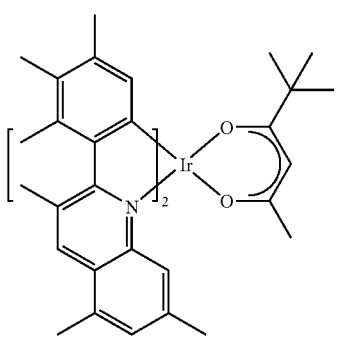
RD-22
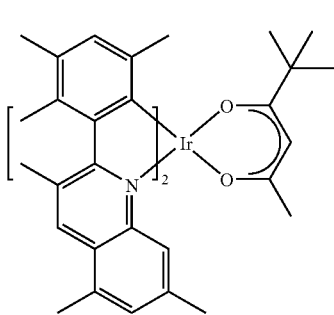
RD-23
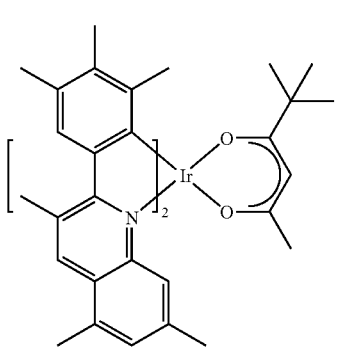
RD-24
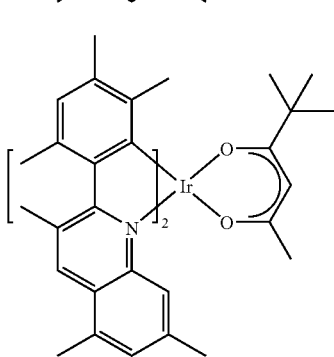
RD-25
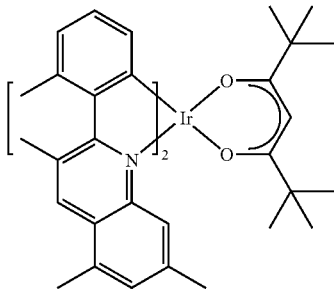

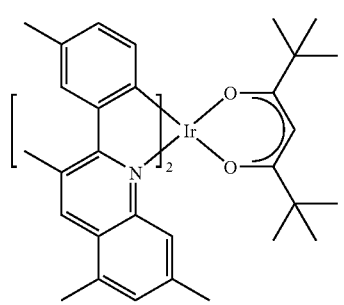 RD-26
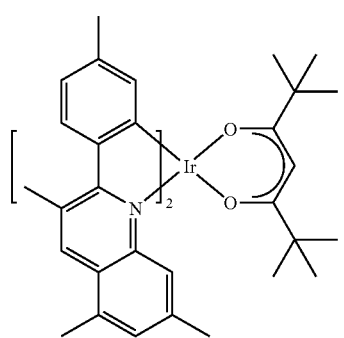 RD-27
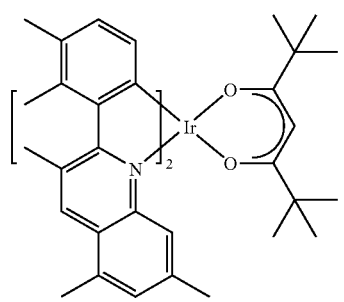 RD-28
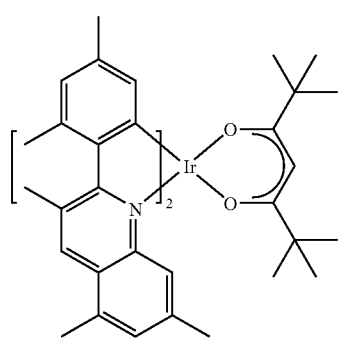 RD-29
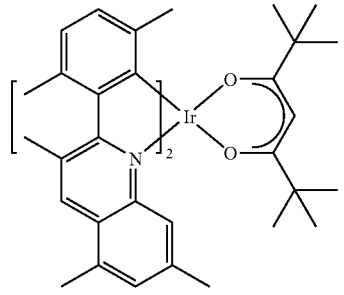 RD-30
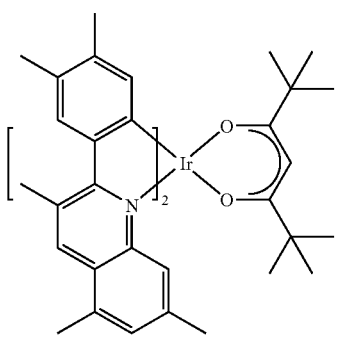 RD-31
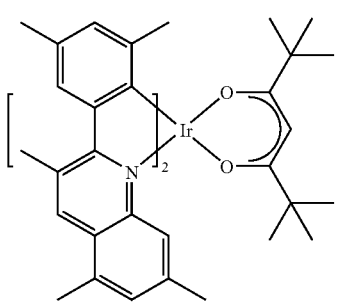 RD-32
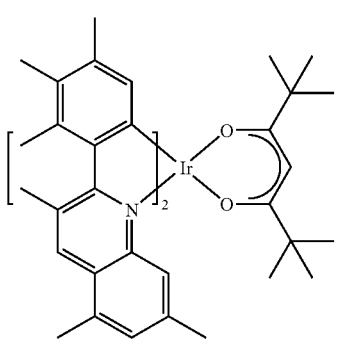 RD-33
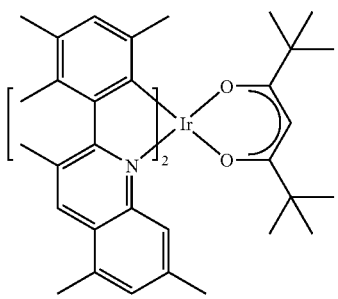 RD-34
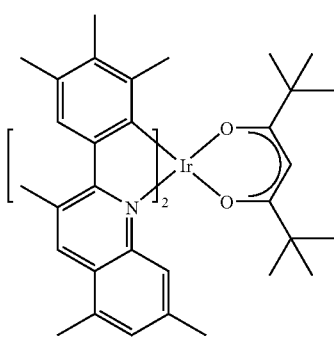 RD-35

-continued

RD-36

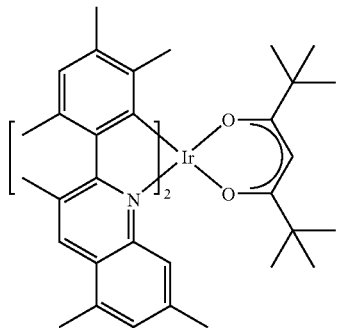

In another aspect of the present invention, there is provided a red phosphorescent compound of Formula 2:

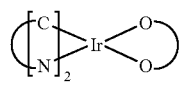
(2)

wherein

is

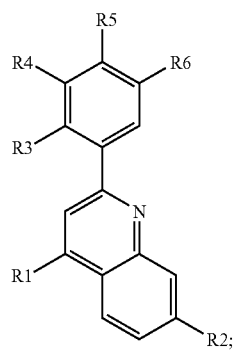

R1 and R2 are independently selected from $C_1$-$C_4$ alkyl groups and $C_1$-$C_4$ alkoxy groups; R3, R4, R5 and R6 are independently selected from hydrogen, $C_1$-$C_4$ alkyl groups and $C_1$-$C_4$ alkoxy groups; and

is selected from 2,4-pentanedione, 2,2,6,6,-tetramethylheptane-3,5-dione, 1,3-propanedione, 1,3-butanedione, 3,5-heptanedione, 1,1,1-trifluoro-2,4-pentanedione, 1,1,1,5,5,5-hexafluoro-2,4-pentanedione and 2,2-dimethyl-3,5-hexanedione.

in Formula 2 is selected from the following compounds:

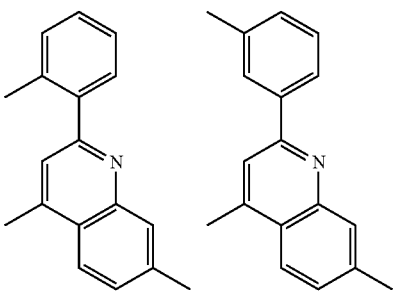

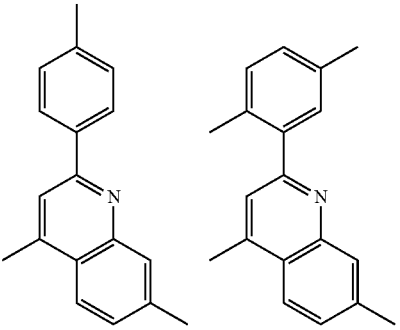
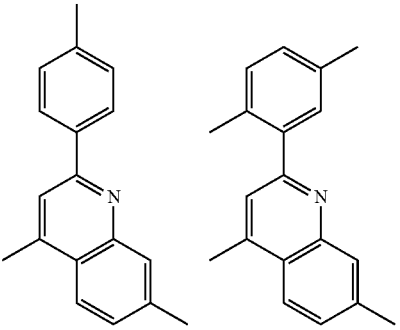

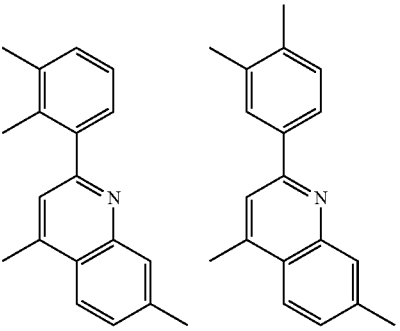
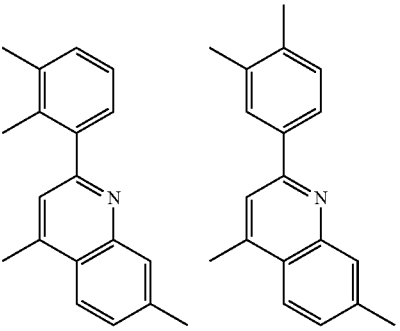

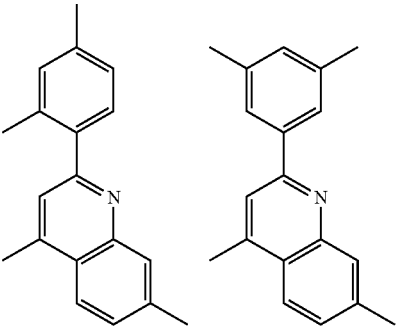

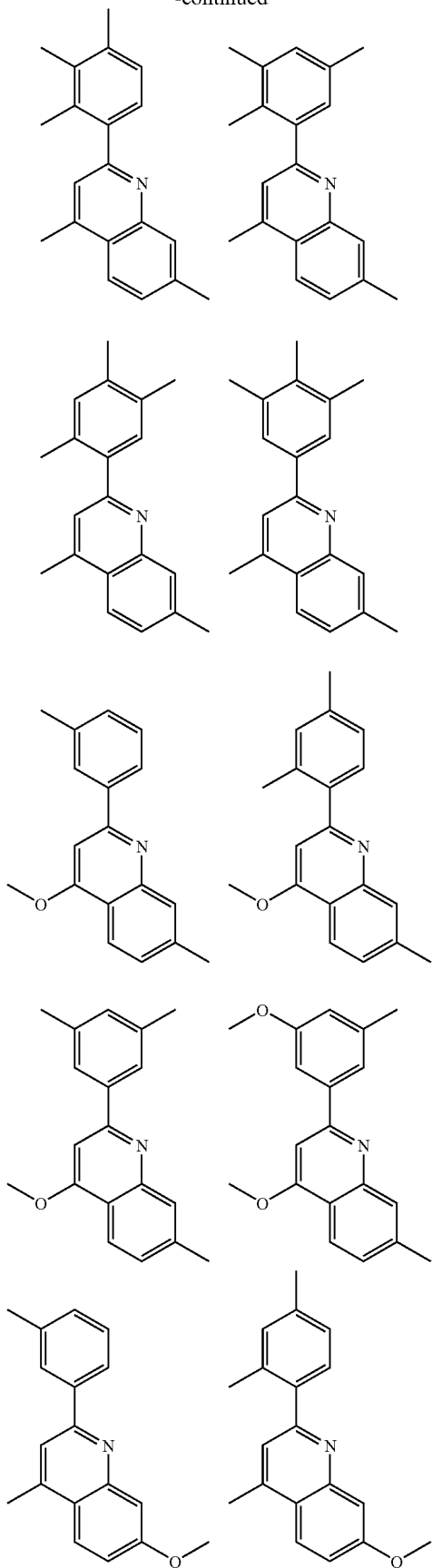
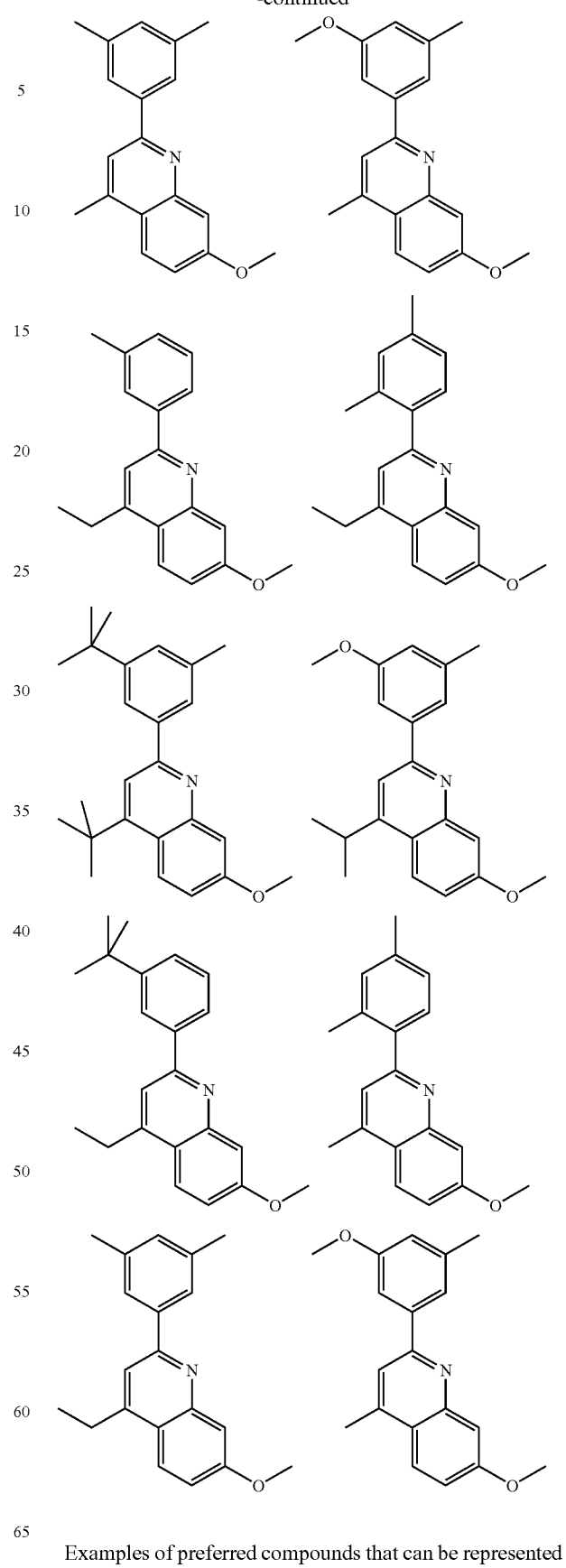
Examples of preferred compounds that can be represented by Formula 2 include the following compounds:

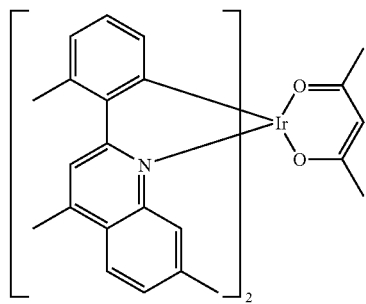
A-1
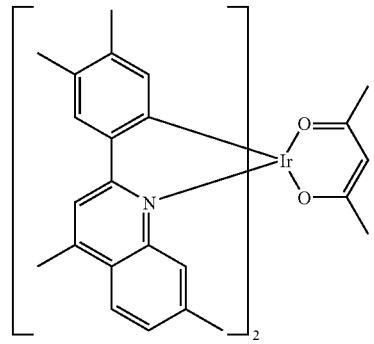
A-6
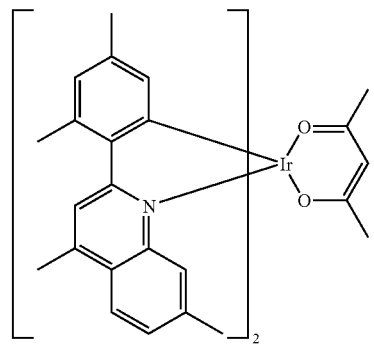
A-7
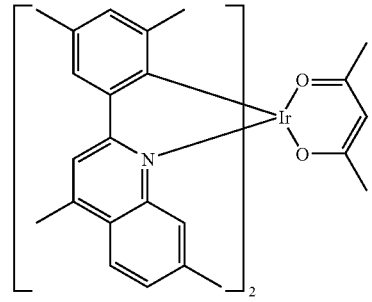
A-8
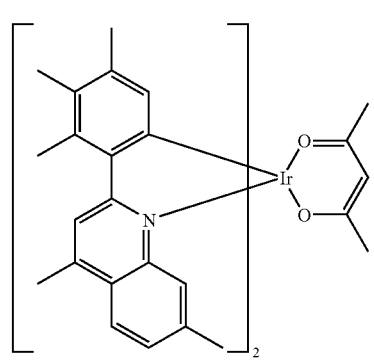
A-9
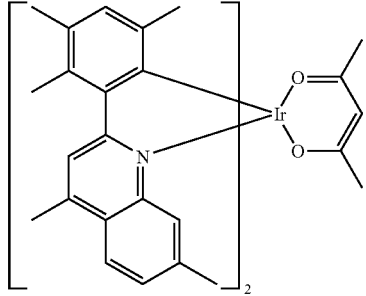
A-10

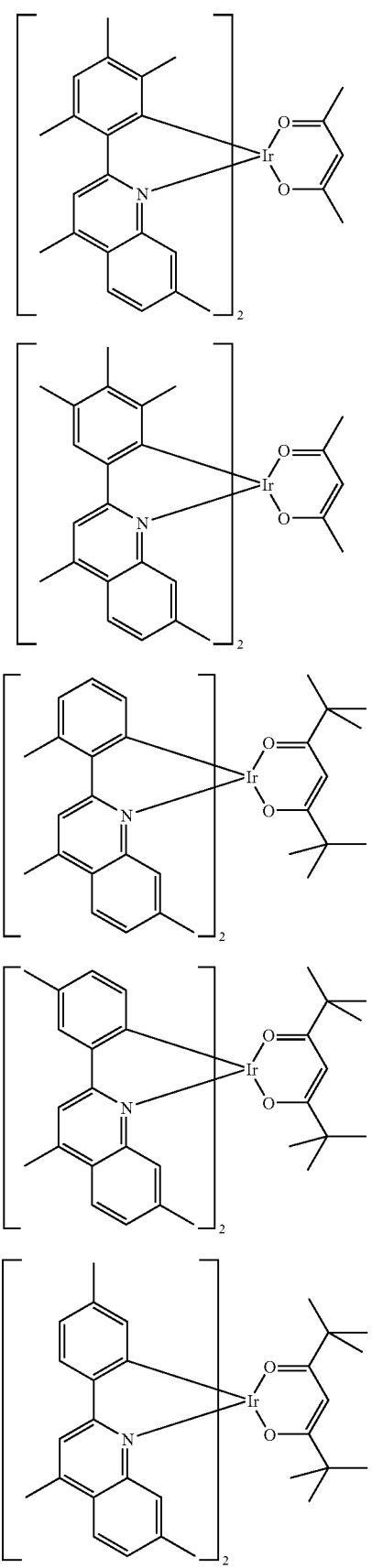
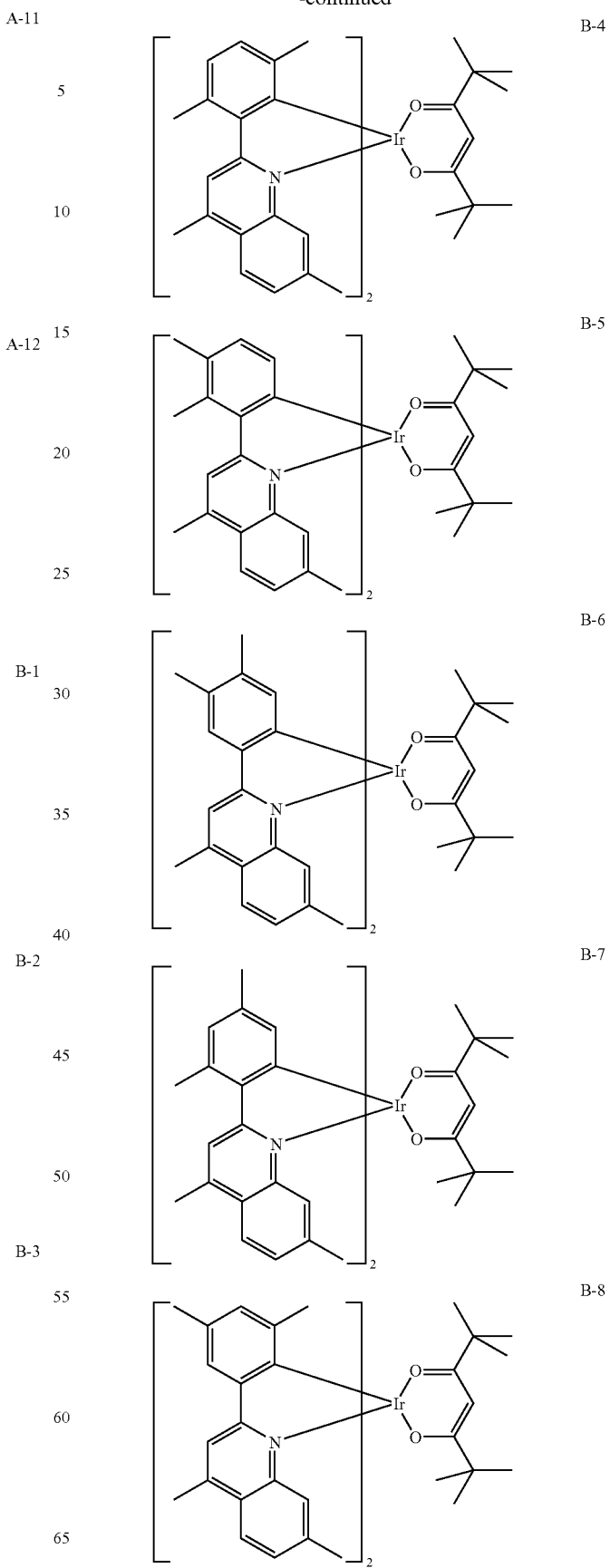

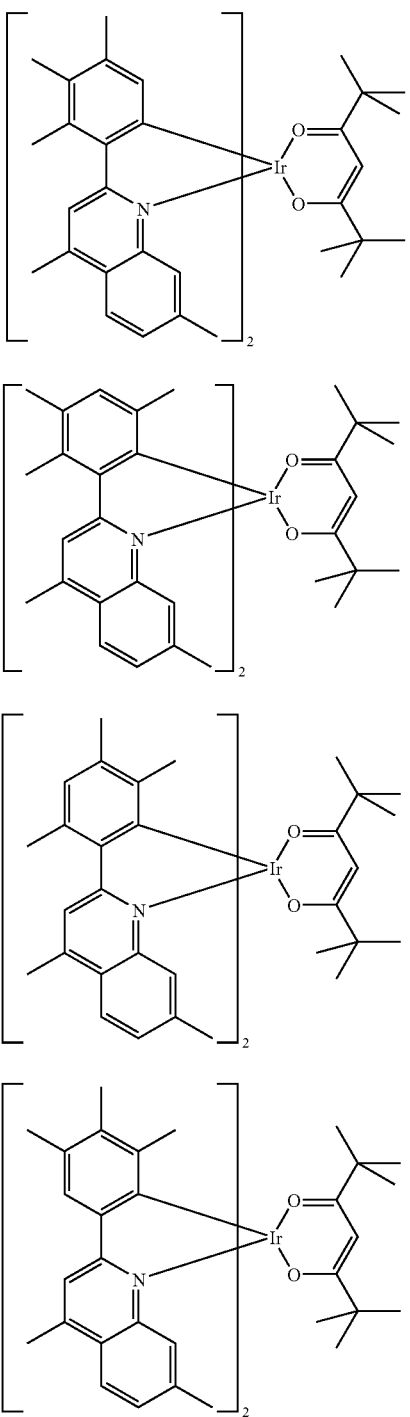

In another aspect of the present invention, there is provided a red phosphorescent compound of Formula 3:

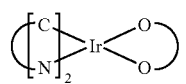

wherein

 is

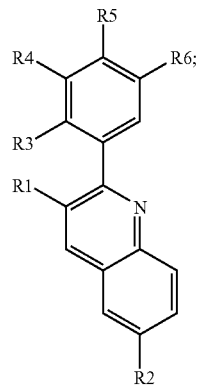

R1 and R2 are independently selected from $C_1$-$C_4$ alkyl groups and $C_1$-$C_4$ alkoxy groups; R3, R4, R5 and R6 are independently selected from hydrogen, $C_1$-$C_4$ alkyl groups and $C_1$-$C_4$ alkoxy groups; and

is selected from 2,4-pentanedione, 2,2,6,6,-tetramethylheptane-3,5-dione, 1,3-propanedione, 1,3-butanedione, 3,5-heptanedione, 1,1,1-trifluoro-2,4-pentanedione, 1,1,1,5,5,5-hexafluoro-2,4-pentanedione and 2,2-dimethyl-3,5-hexanedione.

in Formula 3 is selected from the following compounds:

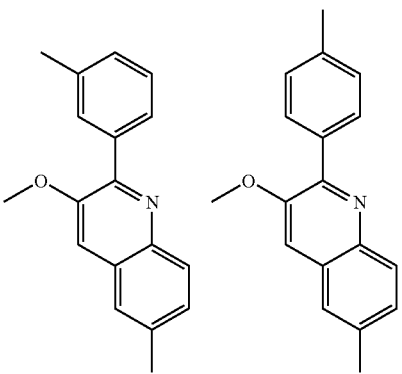

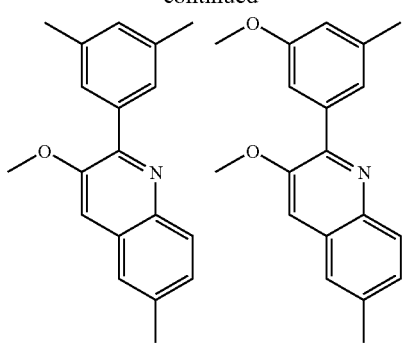
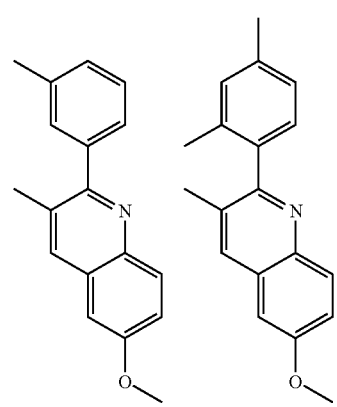
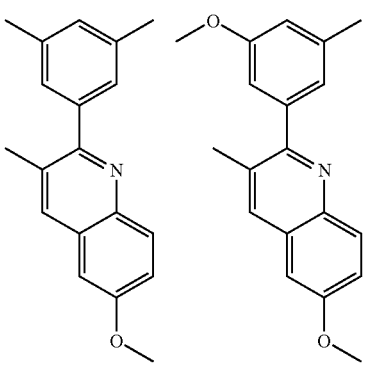
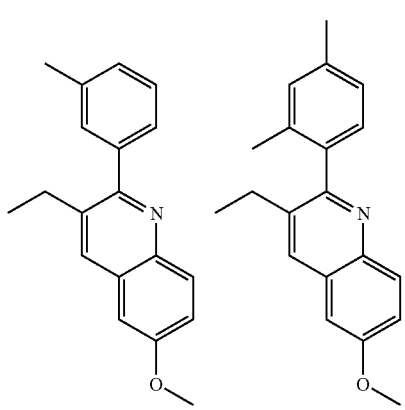
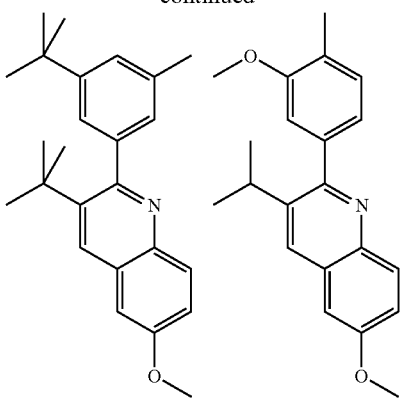
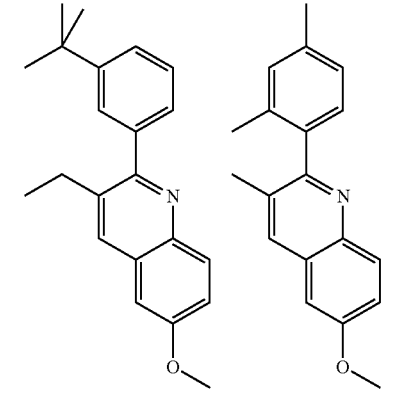
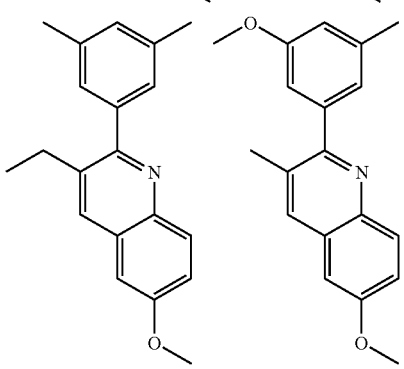
Examples of preferred compounds that can be represented by Formula 3 include the following compounds:
A-1
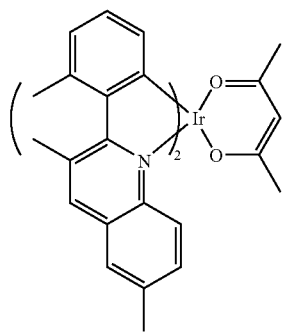

A-2
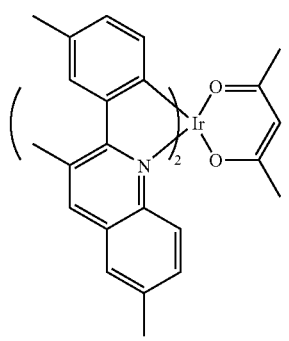
A-3
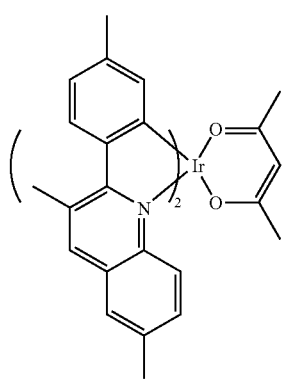
A-4
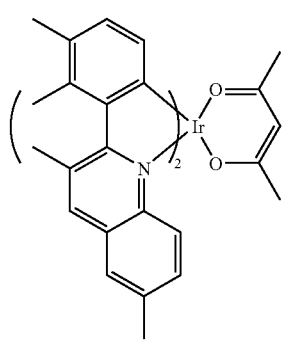
A-5
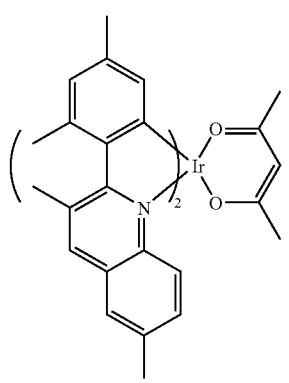
A-6
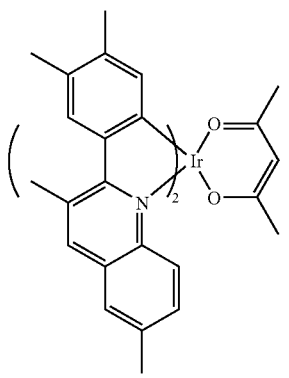
A-7
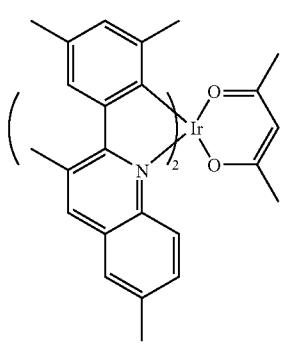
A-8
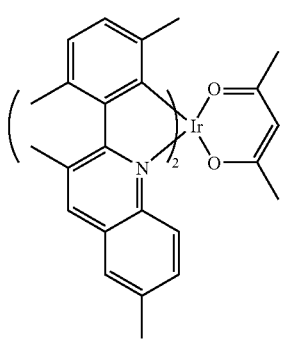
A-9
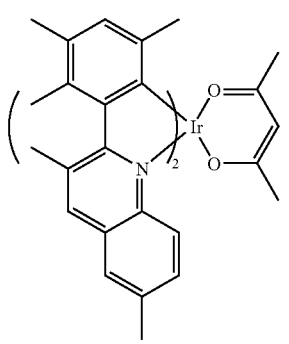

A-10
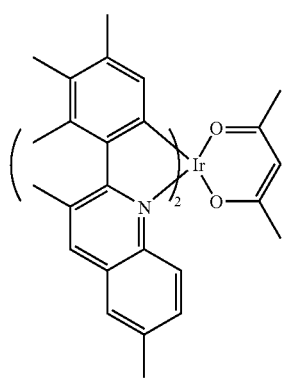
A-11
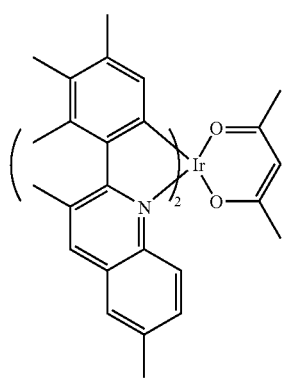
A-12
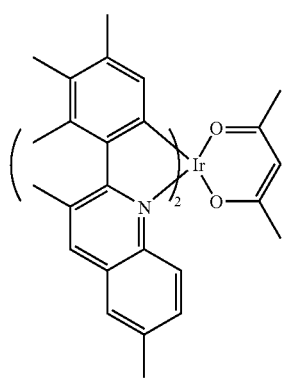
A-13
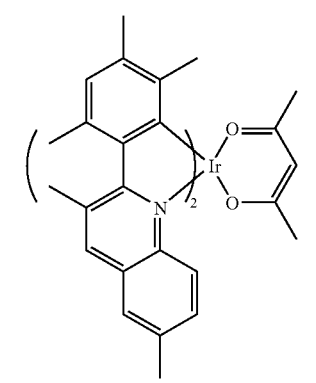
A-14
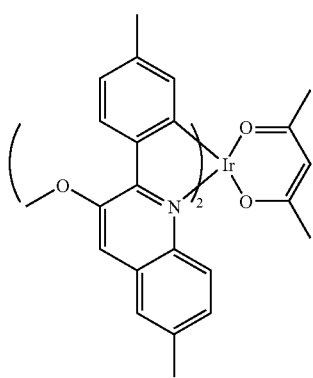
A-15
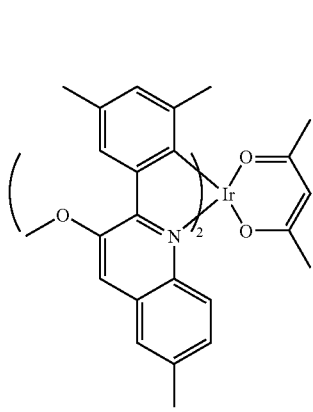
A-16
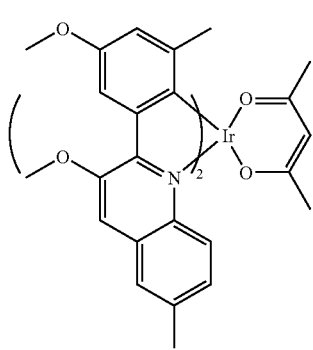
A-17
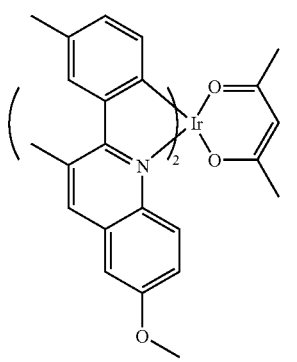

A-18
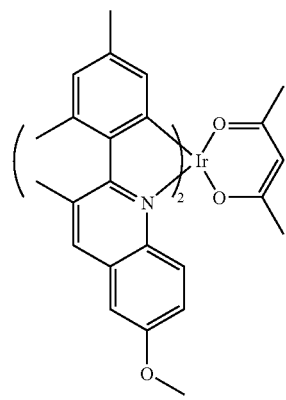
A-19
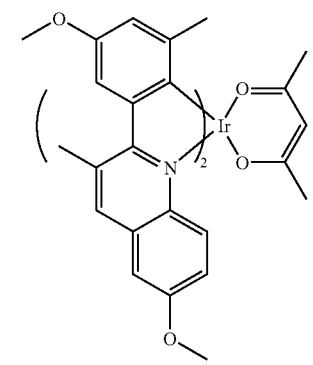
A-20
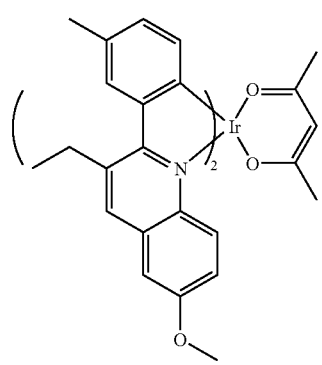
A-21
A-22
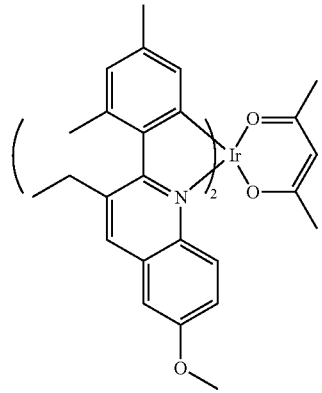
A-23
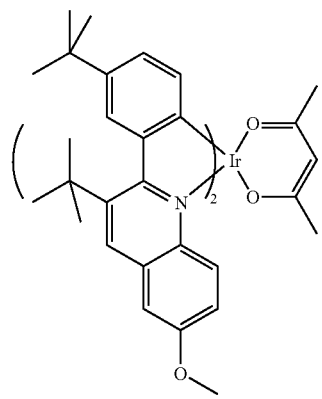
A-24
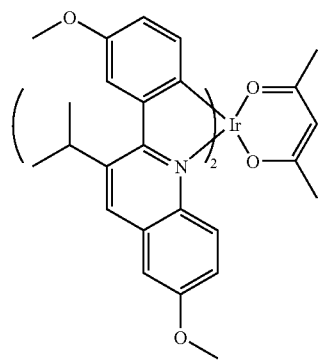
A-25
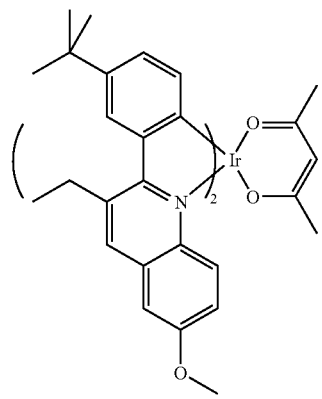

-continued

A-26
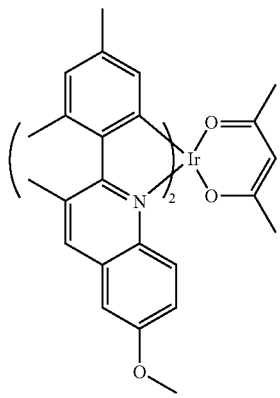

A-27
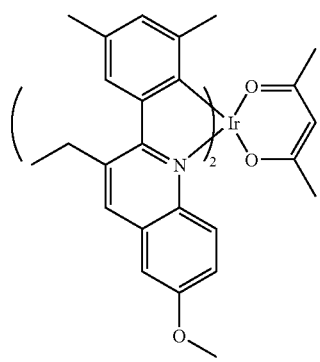

A-28
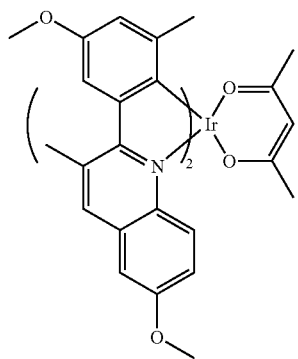

In another aspect of the present invention, there is provided a red phosphorescent compound of Formula 4:

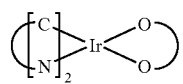  (4)

wherein

is

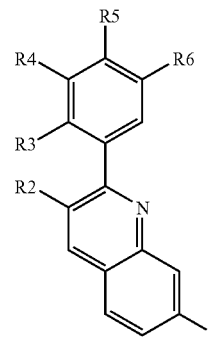

R1 and R2 are independently selected from $C_1$-$C_4$ alkyl groups and $C_1$-$C_4$ alkoxy groups; R3, R4, R5 and R6 are independently selected from hydrogen, $C_1$-$C_4$ alkyl groups and $C_1$-$C_4$ alkoxy groups; and

is selected from 2,4-pentanedione, 2,2,6,6,-tetramethylheptane-3,5-dione, 1,3-propanedione, 1,3-butanedione, 3,5-heptanedione, 1,1,1-trifluoro-2,4-pentanedione, 1,1,1,5,5,5-hexafluoro-2,4-pentanedione and 2,2-dimethyl-3,5-hexanedione.

in Formula 4 is selected from the following compounds:

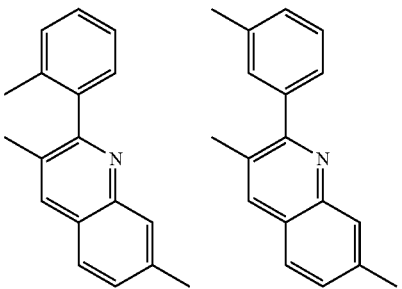

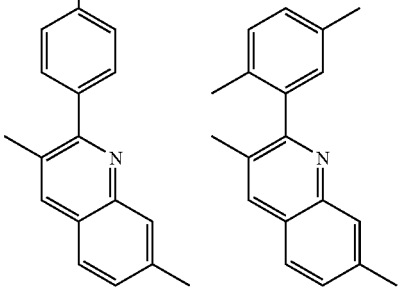

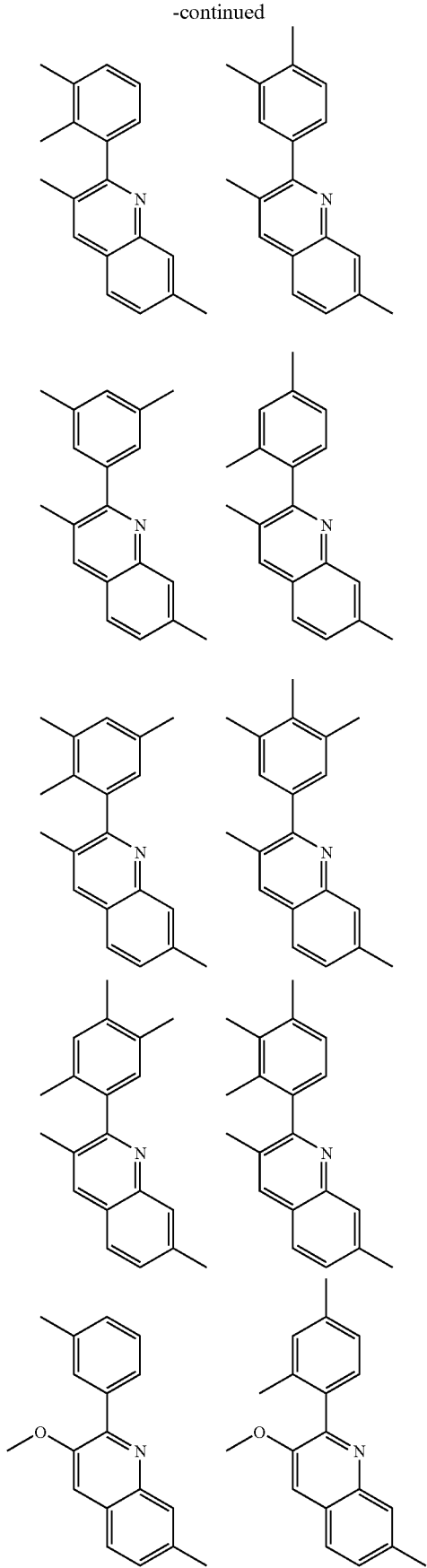
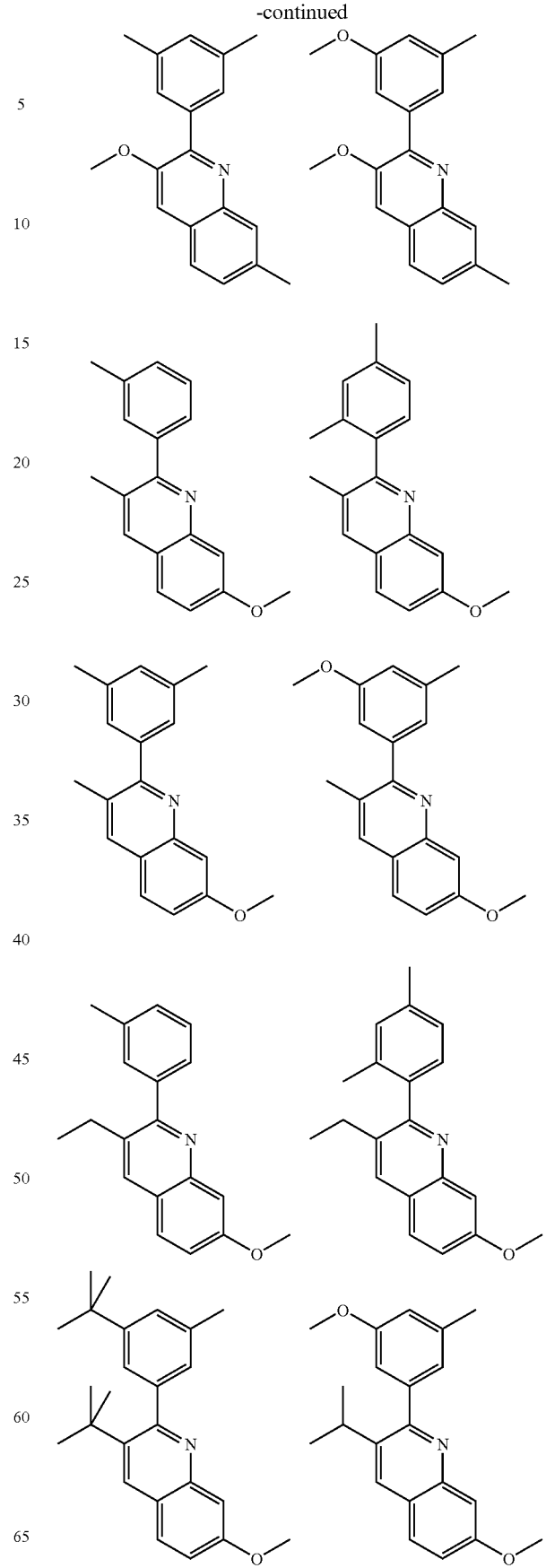

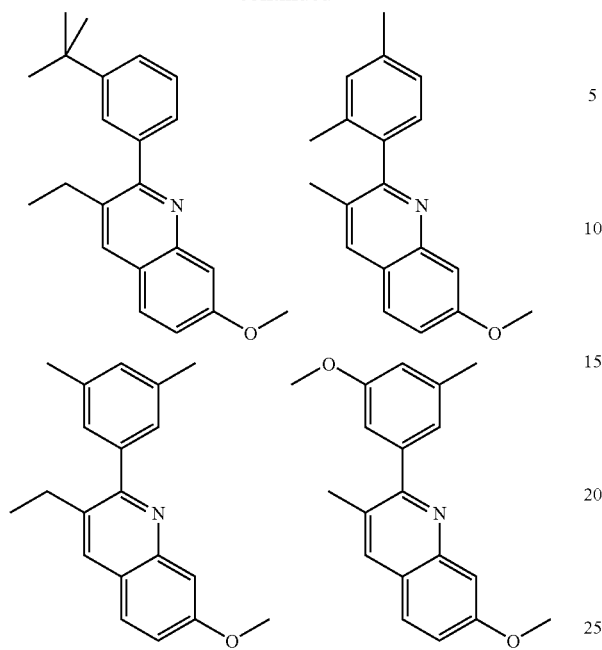
Examples of preferred compounds that can be represented by Formula 4 include the following compounds:
A-1
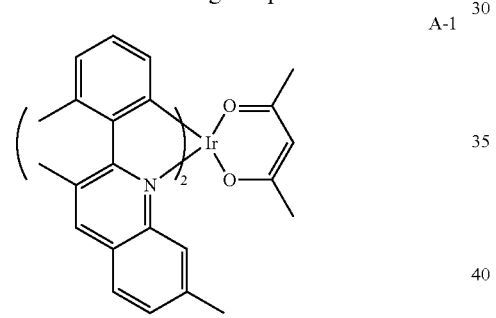
A-2
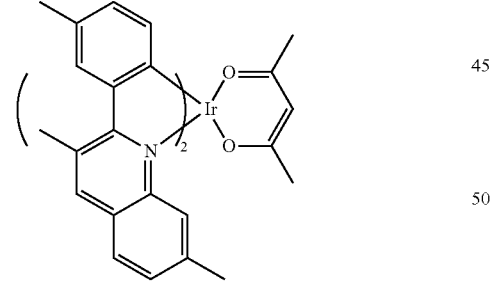
A-3
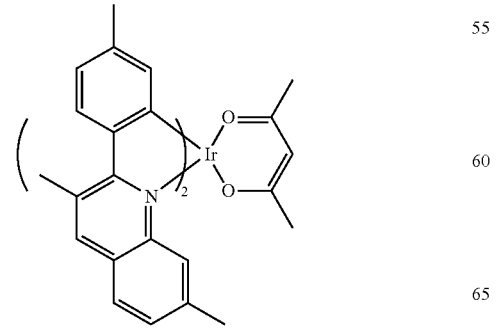
A-4
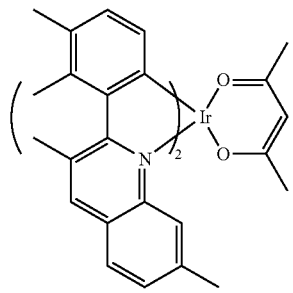
A-5
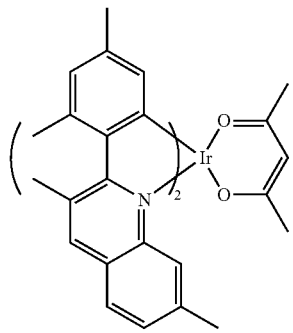
A-6
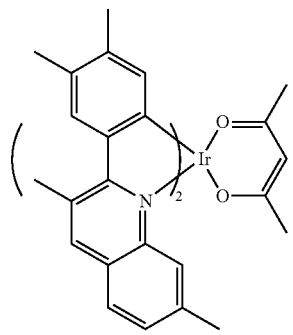
A-7
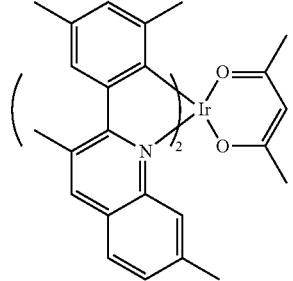
A-8
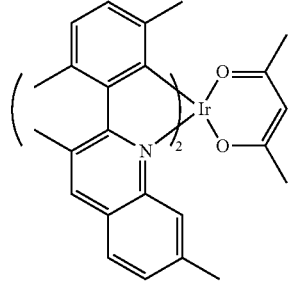

A-9
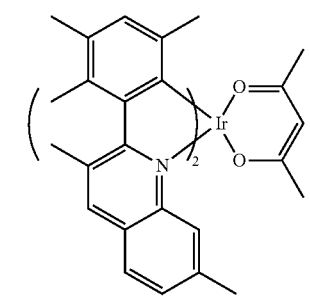
A-10
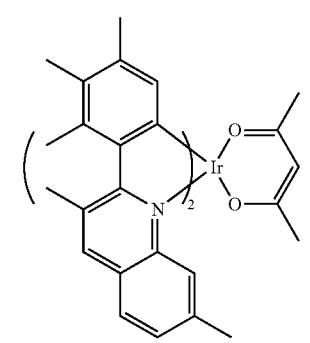
A-11
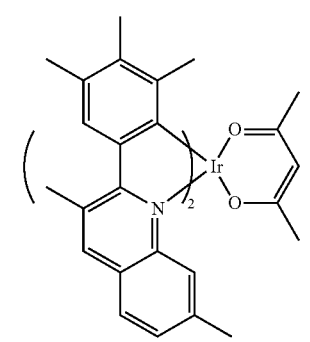
A-12
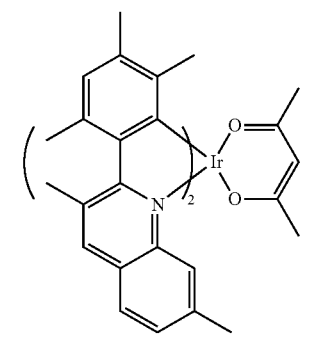
A-13
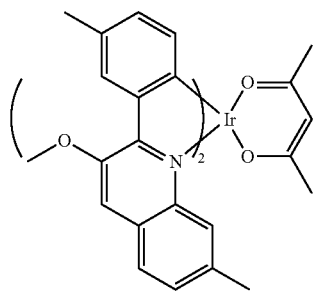
A-14
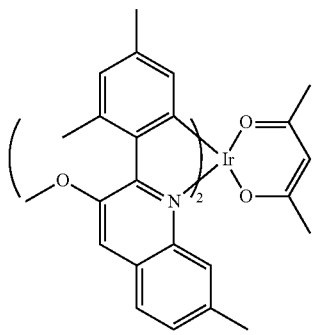
A-15
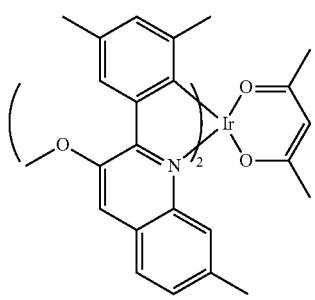
A-16
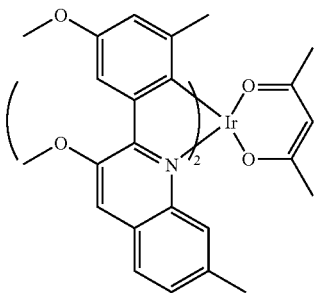
A-17
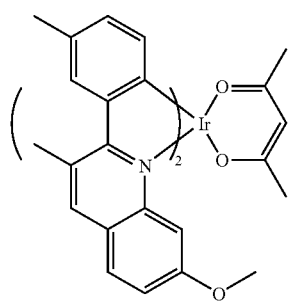
A-18
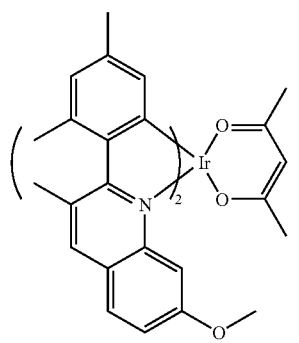

A-19
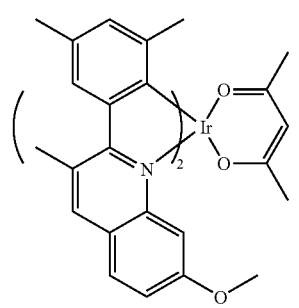
A-20
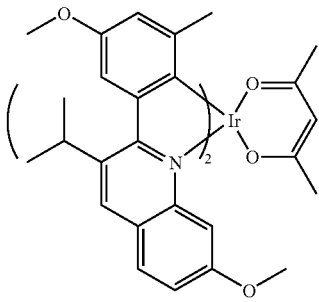
A-21
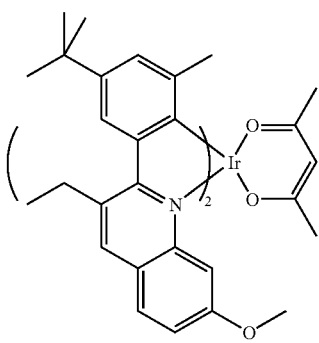
A-22
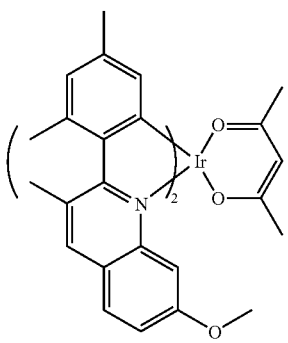
A-23
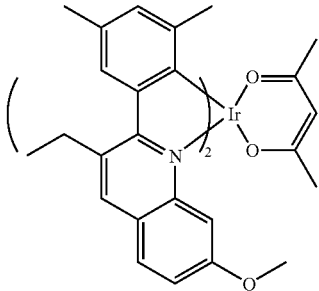
A-24
A-25
A-26
A-27
A-28
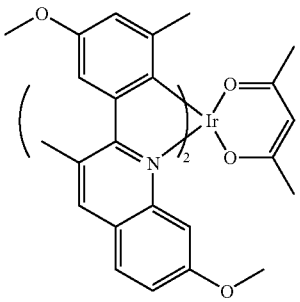

B-1
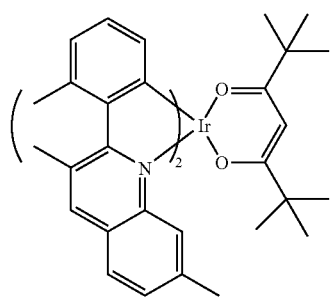
B-2
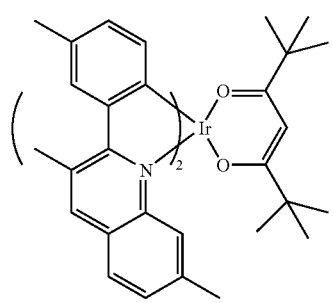
B-3
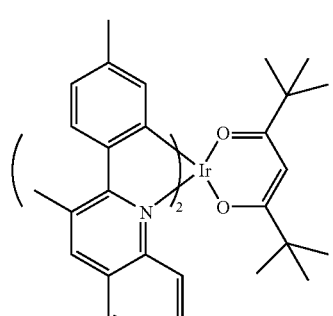
B-4
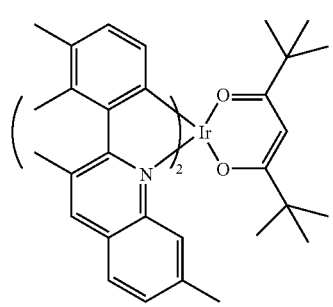
B-5
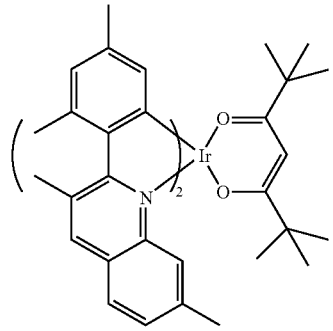
B-6
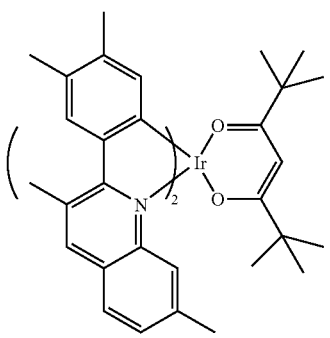
B-7
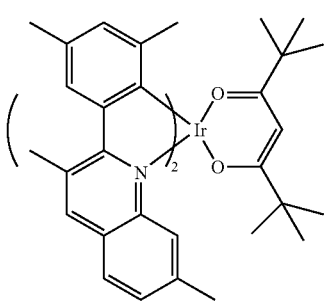
B-8
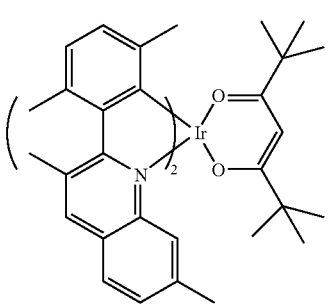
B-9
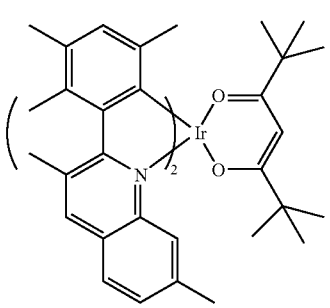
B-10
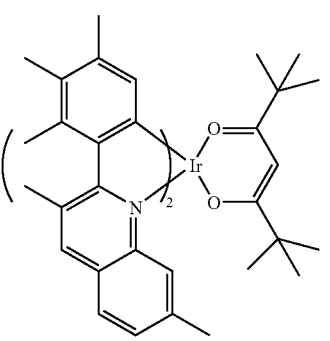

-continued

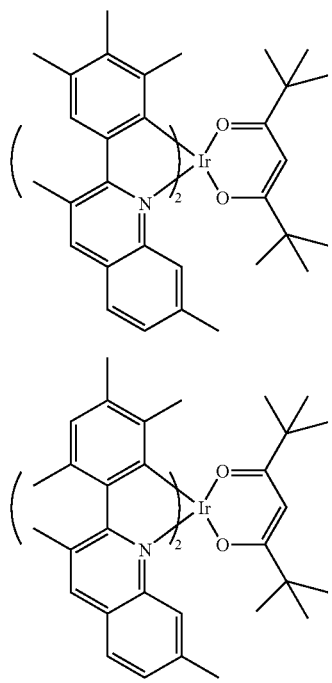

B-11

B-12

In yet another aspect of the present invention, there is provided an organic electroluminescent (EL) device comprising an anode, a hole injecting layer (HIL), a hole transport layer (HTL), an organic light-emitting layer, an electron transport layer (ETL) and an electron injecting layer (EIL), and a cathode laminated in this order wherein one of the red phosphorescent compounds of Formulas 1 to 4 is used as a dopant of the organic light-emitting layer.

A host used in the organic light-emitting layer of the organic EL device according to the present invention may be selected from Al complexes, Zn complexes, and carbazole derivatives. The dopant may be preferably used in an amount of 0.5 to 20% by weight, based on the weight of the host. When the dopant is used within this range, the desired effects of the organic EL device can be achieved. The Al and Zn complexes may have at least one ligand selected from quinolyl, biphenyl, isoquinolyl, phenyl, naphthyl, methylquinolyl, dimethylquinolyl and dimethylisoquinolyl groups. The carbazole derivatives may be preferably 4,4'-N, N'dicarbazole biphenyl (CBP).

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Figure 1:
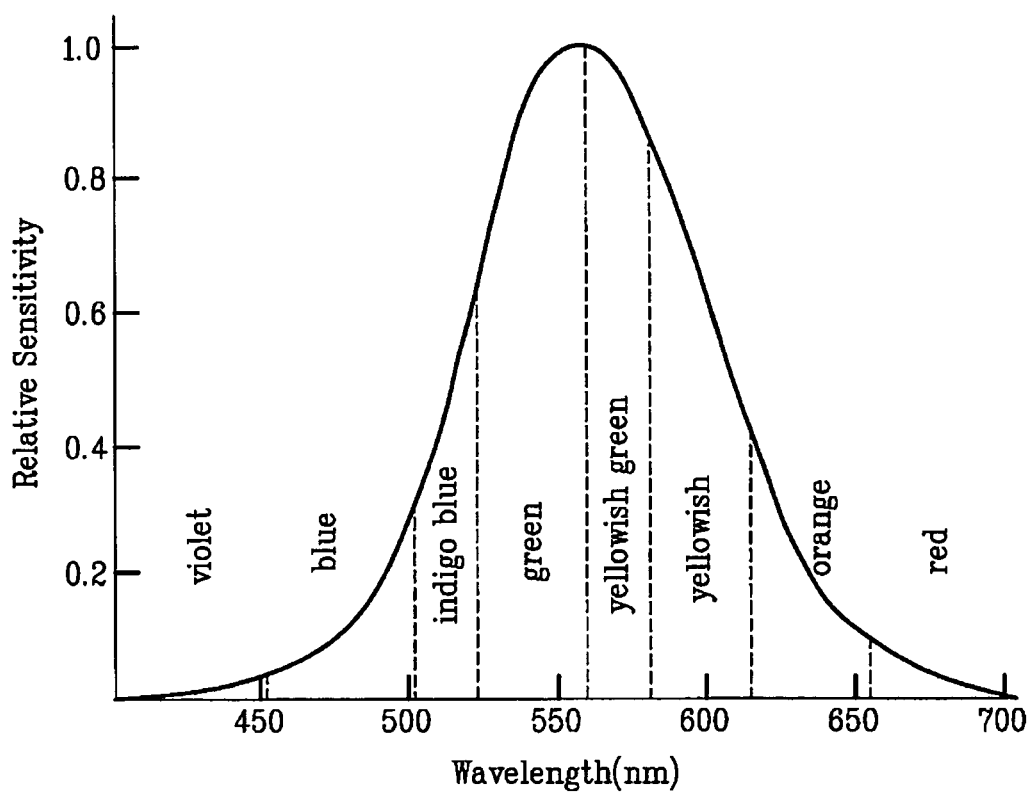
FIG. 1 shows a graph showing a phenomenon wherein the color purity of an organic EL device becomes higher (i.e. as the x-values on CIE chromaticity coordinates increase), the relative sensitivity of the organic EL device decreases.
Figure 2:
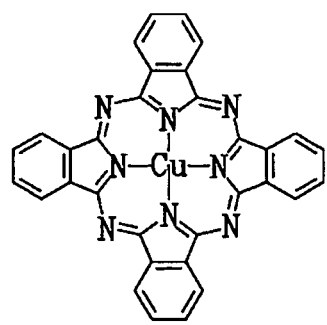
FIG. 2 shows the structural formulas of NPB, copper (II) phthalocyanine (CuPc), (btp)$_2$Ir(acac), Alq$_3$, BAlq and CBP used in Example Section according to the present invention.
Figure 2:
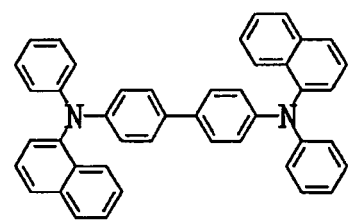
Figure 2:
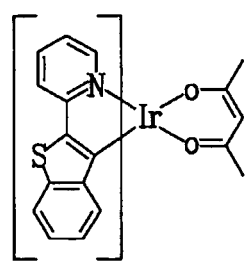
Figure 2:
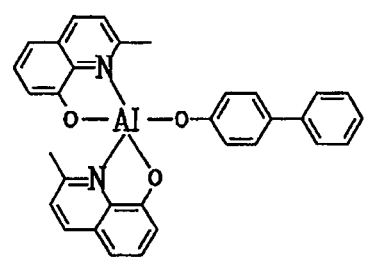
Figure 2:
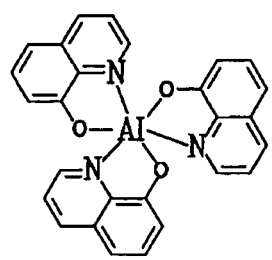
Figure 2:
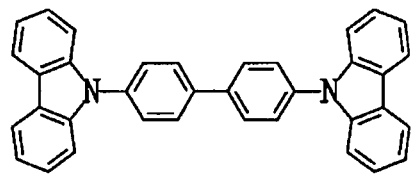

Reference will now be made in detail to the preferred embodiments of the present invention associated with red phosphorescent compounds and an organic electroluminescent (EL) device using one of the red phosphorescent compounds according to the present invention, examples of which are illustrated in the annexed drawings.

Hereinafter, methods for synthesizing the red phosphorescent compounds represented by Formulas 1 to 4 for use in the organic EL devices according to the present invention will be described. First, a method for synthesizing iridium (III) (2-(3'-tolyl)-3,5,7-trimethylquinolinato-N,C$^{2'}$) (2,4-pentanedionate-O,O) ("RD-2"), which is a red phosphorescent compound represented by Formula 1, for use in an organic electroluminescent device.

1. Synthesis of 2-(3'-tolyl)-3,5,7-trimethylquinoline

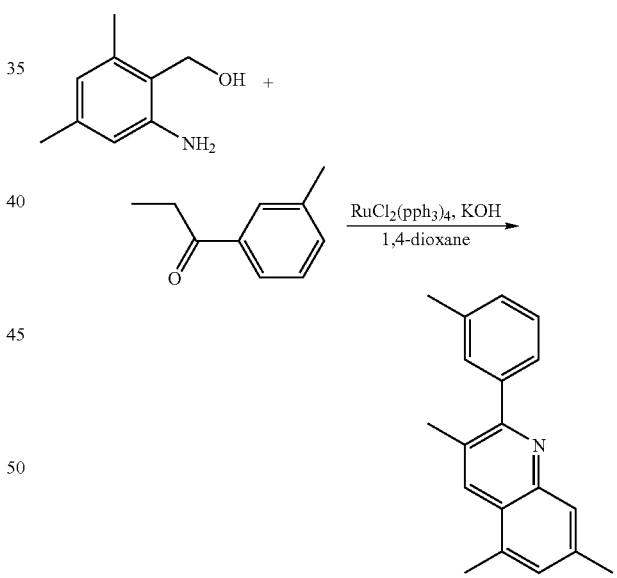

2-Amino-4,6-dimethylbenzylalcohol (5 g, 33 mmol), 1-(3-methylphenyl)-1-propane (9.8 g, 66 mmol), tetrakis(triphenylphosphine)ruthenium chloride (0.3 g, 0.33 mmol) and 1,4-dioxane (50 ml) were put in a dried two-neck round-bottom flask. Then, the mixture was refluxed at 80□ for 3 hours. After the temperature was allowed to cool to room temperature, the mixture was evaporated, and was distilled to yield 2-(3'-tolyl)-3,5,7-trimethylquinoline (7 g, 81%).

2. Synthesis of dichloro-crosslinked dimer complex

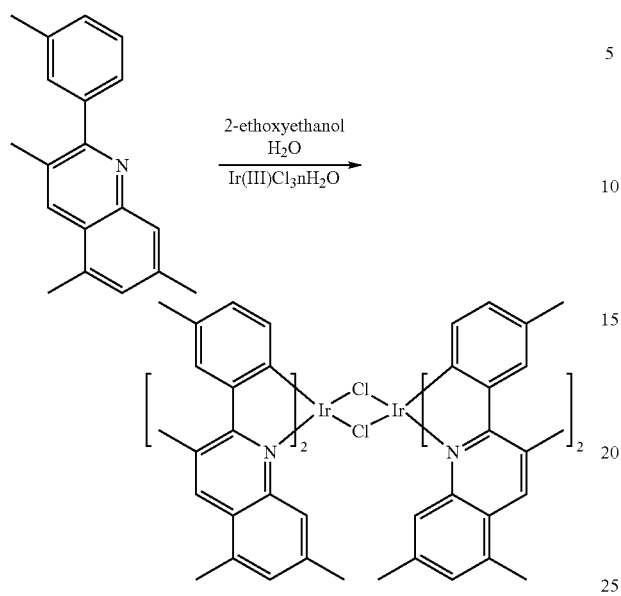

Iridium (III) chloride hydrate (1 g, 3.3 mmol), 2-(3'-tolyl)-3,5,7-trimethylquinoline (1.9 g, 7.3 mmol), 2-ethoxyethanol (30 mL) and water (10 mL) were put in a dried two-neck round-bottom flask. Then, the mixture was refluxed for 12 hours. After the temperature was allowed to cool to room temperature, 30 mL of methanol was added thereto, followed by stirring. The resulting solid was filtered, and was washed with 30 mL of methanol to yield the dichloro-crosslinked dimer complex (3 g, 60%).

3. Synthesis of iridium (III) (2-(3'-tolyl)-3,5,7-trimethylquinolinato-N,C$^{2'}$) (2,4-pentanedionate-O,O)

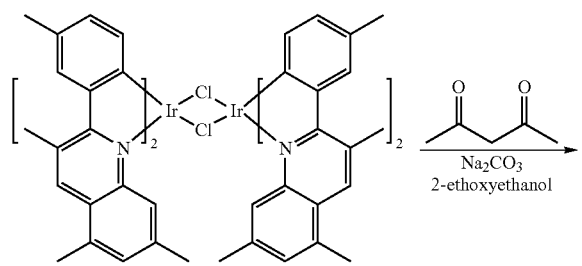

The dichloro-crosslinked dimer complex (2 g, 1.5 mmol), 2,4-pentanedione (0.73 g, 7.5 mmol), sodium carbonate (1.6 g, 15 mmol) and 2-ethoxyethanol (40 mL) were put in a dried two-neck round-bottom flask. Then, the mixture was refluxed for 2 hours. After the temperature was dropped to room temperature, 30 mL of methanol was added thereto, followed by stirring. The resulting solid was filtered and washed with water (30 mL) and methanol (30 mL) to obtain the iridium complex (1.5 g, 70%).

Next, a method for synthesizing iridium (III) (2-(3-methylphenyl)-4,7-dimethylisoquinolinato-N,C$^{2'}$) (2,4-pentanedionate-O,O) ("A-2"), which is a red phosphorescent compound represented by Formula 2, for use in an organic electroluminescent device.

1. Synthesis of 2-(3-methylphenyl)-4,7-dimethylquinoline

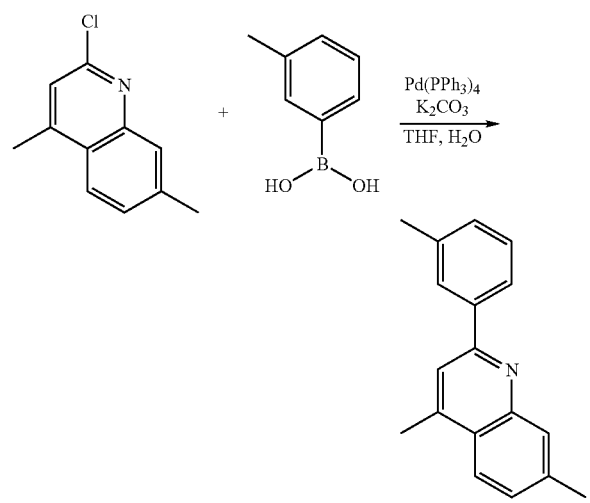

3-Methylphenyl borate (1.3 mmol), 2-chloro-4,6-dimethylquinoline (1 mmol), tetrakis(triphenylphosphine)palladium(O) (0.05 mmol) and potassium carbonate (3 mmol) were dissolved in THF (30 mL) and H$_2$O (10 mL). The resulting solution was stirred in a bath at 100° C. for 24 hours. After completion of the reaction, the solvents were removed. The reaction mixture was extracted with dichloromethane and water and distilled under reduced pressure. The resulting residue was purified by silica gel column chromatography. The eluate was distilled under reduced pressure. The residue was recrystallized from dichloromethane and petroleum ether, and filtered to yield 2-(3-methylphenyl)-4,7-dimethylquinoline as a solid.

2. Synthesis of dichloro-crosslinked dimer complex

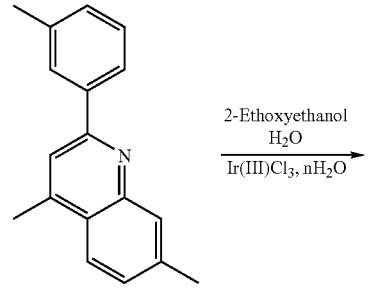

1. Synthesis of 2-chloro-3,6-dimethylquinoline

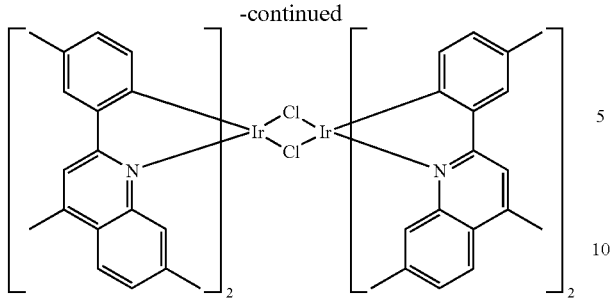

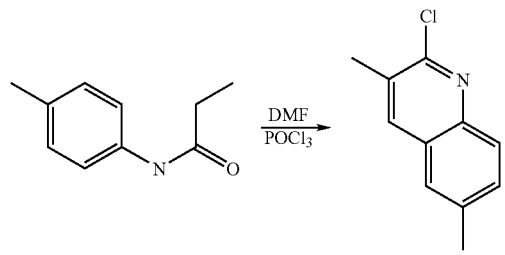

Iridium (III) chloride hydrate (1 mmol), 2-(3-methylphenyl)-4,7-dimethylquinoline (2.5 mmol) and a mixed solvent (30 mL) of 2-ethoxyethanol and distilled water (3:1 (v/v) were put in a dried two-neck round-bottom flask. After the mixture was refluxed for 24 hours, water was added thereto to obtain a solid. The solid was filtered and washed with methanol and petroleum ether to yield the dichloro-crosslinked dimer complex.

3. Synthesis of iridium (III) (2-(3'-tolyl)-3,5,7-trimethylquinolinato-N,C$^{2'}$) (2,4-pentanedionate-O,O)

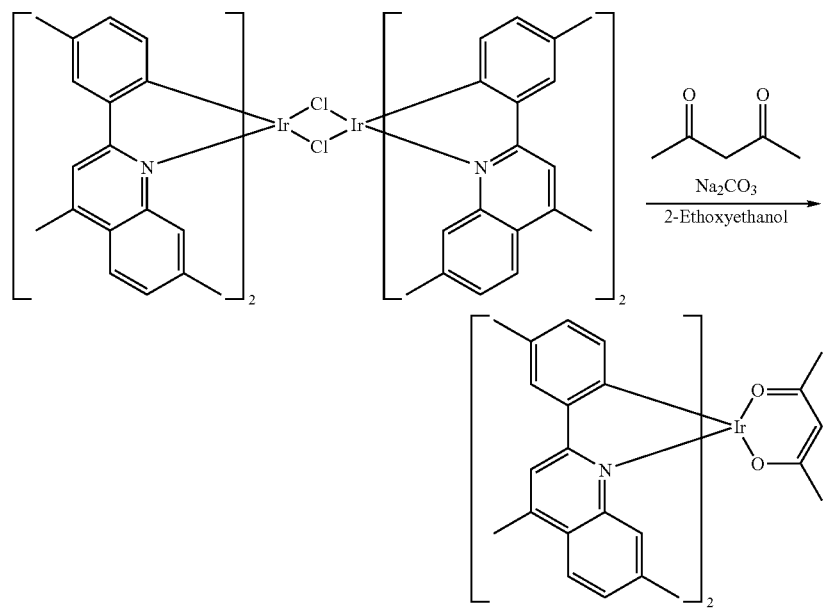

The dichloro-crosslinked dimer complex (1 mmol), 2,4-pentanedione (3 mmol), sodium carbonate (Na$_2$CO$_3$) (6 mmol) and 2-ethoxyethanol (30 mL) were put in a dried two-neck round-bottom flask. Then, the mixture was refluxed for 24 hours. The reaction mixture was allowed to cool to room temperature, and then distilled water was added thereto to obtain a solid. The solid was filtered and dissolved in dichloromethane. The solution was filtered through silica gel. The solvent was distilled off under reduced pressure and the resulting residue was washed with methanol and petroleum ether to yield iridium (III) (2-(3'-tolyl)-3,5,7-trimethylquinolinato-N,C$^{2'}$) (2,4-pentanedionate-O,O).

Next, a method for synthesizing iridium (III) (2-(3-methylphenyl)-3,6-dimethylquinolinato-N,C$^{2'}$) (2,4-pentanedionate-O,O) ("A-2"), which is a red phosphorescent compound represented by Formula 3, for use in an organic electroluminescent device.

N-(4-methylphenyl)-propionamide (5 mmol) and a solution of DMF (1.5 M) in POCl$_3$ (7 M) were put in a dried two-neck round-bottom flask. Then, the mixture was stirred in a bath at 75° C. for 4 hours. After completion of the reaction, the DMF was removed. The reaction mixture was extracted with dichloromethane and water. The extract was distilled under reduced pressure. The resulting residue was purified by silica gel column chromatography. The eluate was distilled under reduced pressure. The residue was recrystallized from dichloromethane and petroleum ether and filtered to yield 2-chloro-3,6-dimethylquinoline as a solid.

2. synthesis of 2-(3-methylphenyl)-3,6-dimethylquinoline

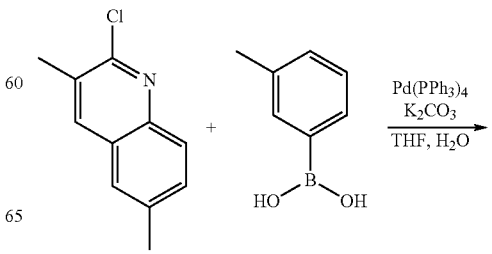

4. Synthesis of iridium (III) (2-(3-methylphenyl-3,6-dimethylquinolinato-N,C$^{2'}$) (2,4-pentanedionate-O,O)

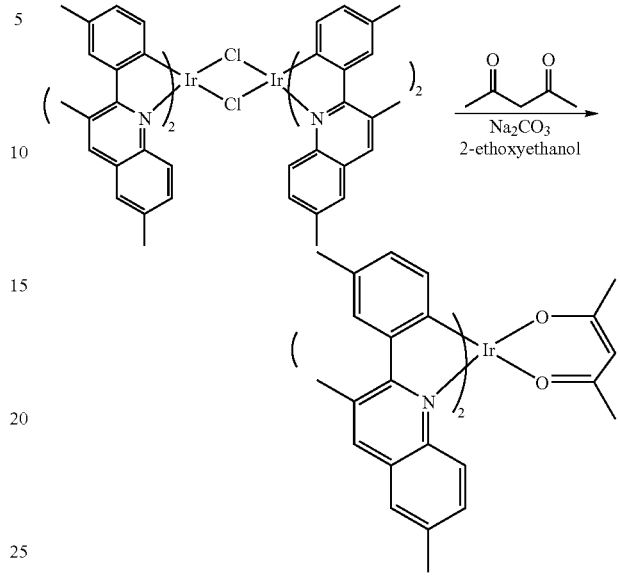

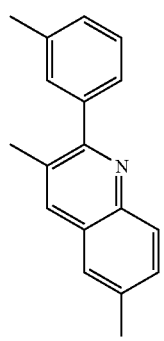

3-Methylphenyl borate (1.3 mmol), 2-chloro-3,6-dimethylquinoline (1 mmol), tetrakis(triphenylphosphine)palladium(O) (0.05 mmol) and potassium carbonate (3 mmol) were dissolved in THF (30 mL) and H$_2$O (10 mL). The resulting solution was stirred in a bath at 100° C. for 24 hours. After completion of the reaction, the THF and the toluene were removed. The reaction solution was extracted with dichloromethane and water, and distilled under reduced pressure. The resulting residue was purified by silica gel column chromatography. The eluate was distilled under reduced pressure. The residue was recrystallized from dichloromethane and petroleum ether and filtered to yield 2-(3-methylphenyl)-3,6-dimethylquinoline as a solid.

3. Synthesis of dichloro-crosslinked dimer complex

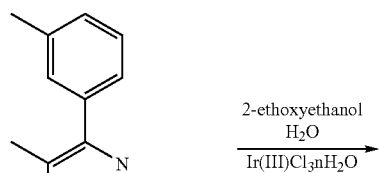

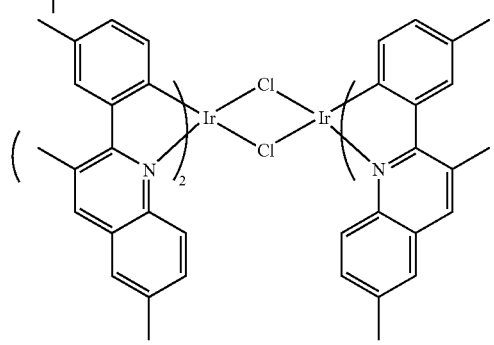

Iridium (III) chloride hydrate (1 mmol), 2-(3-methylphenyl)-3,6-dimethylquinoline (2.5 mmol) and a mixed solvent (30 mL) of 2-ethoxyethanol and distilled water (3:1) were put in a dried two-neck round-bottom flask. After the mixture was refluxed for 24 hours, water was added thereto to obtain a solid. The solid was filtered and washed with methanol and petroleum ether to yield the dichloro-crosslinked dimer complex.

The dichloro-crosslinked dimer complex (1 mmol), 2,4-pentanedione (3 mmol), sodium carbonate (Na$_2$CO$_3$) (6 mmol) and 2-ethoxyethanol (30 mL) were put in a dried two-neck round-bottom flask. Then, the mixture was refluxed for 24 hours. After the mixture was allowed to cool to room temperature, distilled water was added thereto to obtain a solid. The solid was filtered and dissolved in dichloromethane. The solution was filtered through silica gel. The solvent was distilled off under reduced pressure and the residue was washed with methanol and petroleum ether to yield 2-(3-methylphenyl-3,6-dimethylquinolinato-N,C$^{2'}$) (2,4-pentanedionate-O,O).

Lastly, a method for synthesizing iridium (III) (2-(3-methylphenyl)-3,7-dimethylquinolinato-N,C$^{2'}$) (2,4-pentanedionate-O,O) ("A-2"), which is a red phosphorescent compound represented by Formula 4, for use in an organic electroluminescent device.

1. Synthesis of 2-chloro-3,7-dimethylquinoline

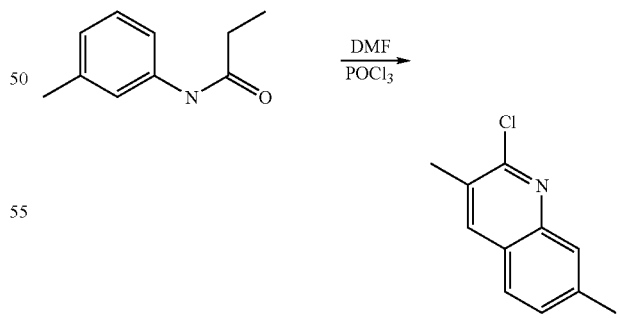

N-(4-methylphenyl)-propionamide (5 mmol) and a solution of DMF (1.5 M) in POCl$_3$ (7 M) were put in a dried two-neck round-bottom flask. Then, the mixture was stirred in a bath at 75° C. for 4 hours. After completion of the reaction, the DMF was removed. The reaction mixture was extracted with dichloromethane and water. The extract was distilled under reduced pressure and purified by silica gel column chromatography. The eluate was distilled under reduced pressure, and recrystallized from dichloromethane and petroleum ether and was filtered to yield 2-chloro-3,7-dimethylquinoline as a solid.

2. synthesis of 2-(3-methylphenyl)-3,7-dimethylquinoline

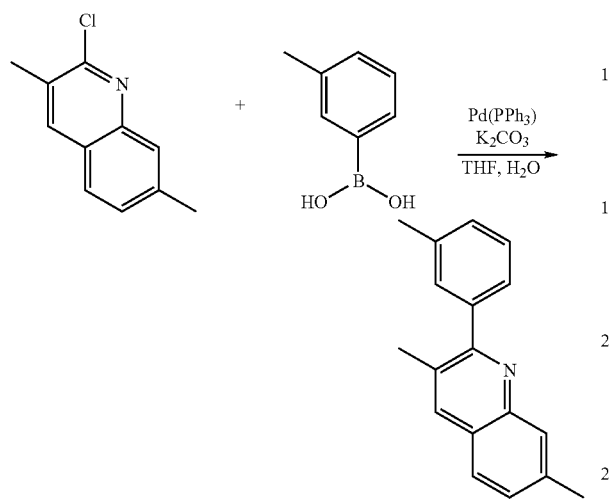

3-Methylphenyl borate (1.3 mmol), 2-chloro-3,7-dimethylquinoline (1 mmol), tetrakis(triphenylphosphine)palladium(O) (0.05 mmol) and potassium carbonate (3 mmol) were dissolved in THF (30 mL) and H$_2$O (10 mL). The resulting solution was stirred in a bath at 100° C. for 24 hours. After completion of the reaction, the THF and the toluene were removed. The reaction mixture was extracted with dichloromethane and water. The extract was distilled under reduced pressure and purified by silica gel column chromatography. The eluate was distilled under reduced pressure and recrystallized from dichloromethane and petroleum ether to obtain a precipitate. The precipitate was filtered to yield 2-(3-methylphenyl)-3,7-dimethylquinoline as a solid.

3. Synthesis of dichloro-crosslinked dimer complex

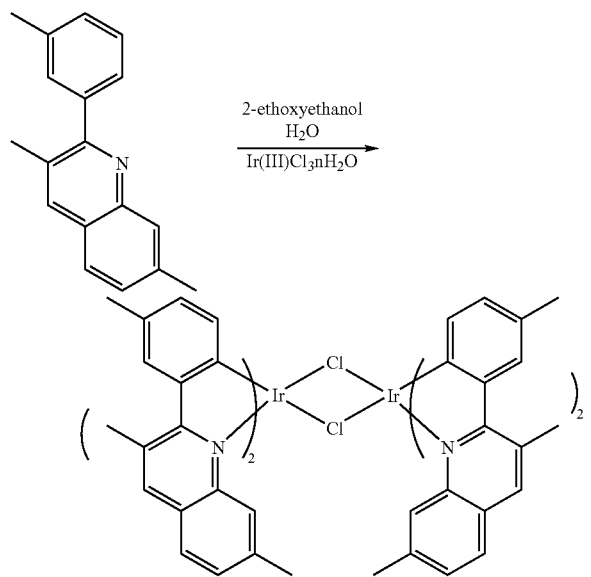

Iridium (III) chloride hydrate (1 mmol), 2-(3-methylphenyl)-3,7-dimethylquinoline (2.5 mmol) and a mixed solvent (30 mL) of 2-ethoxyethanol and distilled water (3:1) were put in a dried two-neck round-bottom flask. After the mixture was refluxed for 24 hours, water was added thereto to obtain a solid. The solid was filtered and was washed with methanol and petroleum ether to yield the dichloro-crosslinked dimer complex.

4. Synthesis of iridium (III) (2-(3-methylphenyl-3,7-dimethylquinolinato-N,C$^{2'}$) (2,4-pentanedionate-O,O)

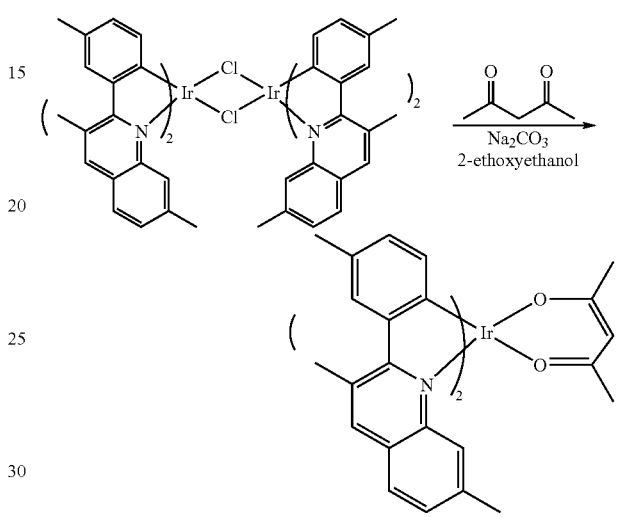

The dichloro-crosslinked dimer complex (1 mmol), 2,4-pentanedione (3 mmol), sodium carbonate (Na$_2$CO$_3$) (6 mmol) and 2-ethoxyethanol (30 mL) were put in a dried two-neck round-bottom flask. Then, the mixture was refluxed for 24 hours. After the reaction mixture was allowed to cool to room temperature, distilled water was added thereto to obtain a solid. The solid was filtered and dissolved in dichloromethane. The solution was filtered through silica gel. The solvent was distilled off under reduced pressure and the residue was washed with methanol and petroleum ether to yield iridium(III)(2-(3'-tolyl)-3,7-trimethylquinolinato-N,C$^{2'}$)(2,4-pentanedionate-O,O).

Hereinafter, a detailed description will be made of preferred examples of the present invention. The invention is not to be construed as being limited to the examples.

EXAMPLES A-1 TO A-5 (COMPOUNDS OF FORMULA 1) AND COMPARATIVE EXAMPLE A-1

Example A-1

An ITO-coated glass substrate was patterned to have a light-emitting area of 3 mm×3 mm, followed by cleaning. After the patterned substrate was disposed in a vacuum chamber, the standard pressure of the chamber was adjusted to 1×10$^{-6}$ torr. CuPc (200 Å), NPD (400 Å), BAlq+RD-2 (7%) (200 Å), Alq$_3$ (300 Å), LiF (5 Å) and Al (1000 Å) were sequentially deposited on the ITO glass substrate to fabricate an organic EL device.

The luminance of the organic EL device was 1,002 cd/m$^2$ at an electric current of 0.9 mA and a voltage of 6.8 V. At this time, the CIE chromaticity coordinates were x=0.651 and y=0.351. The lifetime (defined as the time taken before the luminance of the organic EL device decreases to half its initial value) of the organic EL device was 6,000 hours at 2,000 cd/m².

Example A-2

An ITO-coated glass substrate was patterned to have a light-emitting area of 3 mm×3 mm, followed by cleaning. After the patterned substrate was disposed in a vacuum chamber, the standard pressure of the chamber was adjusted to 1×10⁻⁶ torr. CuPc (200 Å), NPD (400 Å), BAlq+RD-7 (7%) (200 Å), Alq₃ (300 Å), LiF (5 Å) and Al (1000 Å) were sequentially deposited on the ITO glass substrate to fabricate an organic EL device.

The luminance of the organic EL device was 1,034 cd/m² at an electric current of 0.9 mA and a voltage of 6.5 V. At this time, the CIE chromaticity coordinates were x=0.650 and y=0.350. The lifetime (defined as the time taken before the luminance of the organic EL device decreases to half its initial value) of the organic EL device was 5,000 hours at 2,000 cd/m².

Example A-3

An ITO-coated glass substrate was patterned to have a light-emitting area of 3 mm×3 mm, followed by cleaning. After the patterned substrate was disposed in a vacuum chamber, the standard pressure of the chamber was adjusted to 1×10⁻⁶ torr. CuPc (200 Å), NPD (400 Å), BAlq+RD-9 (7%) (200 Å), Alq₃ (300 Å), LiF (5 Å) and Al (1000 Å) were sequentially deposited on the ITO glass substrate to fabricate an organic EL device.

The luminance of the organic EL device was 908 cd/m² at an electric current of 0.9 mA and a voltage of 6.2 V. At this time, the CIE chromaticity coordinates were x=0.655 and y=0.352. The lifetime (defined as the time taken before the luminance of the organic EL device decreases to half its initial value) of the organic EL device was 4,500 hours at 2,000 cd/m².

Example A-4

An ITO-coated glass substrate was patterned to have a light-emitting area of 3 mm×3 mm, followed by cleaning. The patterned substrate was disposed in a vacuum chamber. Then, the standard pressure of the chamber was adjusted to 1×10⁻⁶ torr. CuPc (200 Å), NPD (400 Å), BAlq+RD-14 (7%) (200 Å), a hole blocking layer (100 Å), Alq₃ (300 Å), LiF (5 Å) and Al (1000 Å) were sequentially deposited on the ITO glass substrate to manufacture an organic EL device.

When BAlq was used as a material for the hole blocking layer, the luminance of the organic EL device was 940 cd/m² at an electric current of 0.9 mA and a voltage of 6.9 V. At this time, the CIE chromaticity coordinates were x=0.653, y=0.351. The lifetime (defined as the time taken before the luminance of the organic EL device decreases to half its initial value) of the organic EL device was 3,500 hours at 2,000 cd/m².

Example A-5

An ITO-coated glass substrate was patterned to have a light-emitting area of 3 mm×3 mm, followed by cleaning. The patterned substrate was disposed in a vacuum chamber. Then, the standard pressure of the chamber was adjusted to 1×10⁻⁶ torr. CuPc (200 Å), NPD (400 Å), BAlq+RD-26 (7%) (200 Å), a hole blocking layer (100 Å), Alq₃ (300 Å), LiF (5 Å) and Al (1000 Å) were sequentially deposited on the ITO glass substrate to manufacture an organic EL device.

When BAlq was used as a material for the hole blocking layer, the luminance of the organic EL device was 955 cd/m² at an electric current of 0.9 mA and a voltage of 7.0 V. At this time, the CIE chromaticity coordinates were x=0.656 and y=0.353. The lifetime (defined as the time taken before the luminance of the organic EL device decreases to half its initial value) of the organic EL device was 4,000 hours at 2,000 cd/m².

Comparative Example A-1

An ITO-coated glass substrate was patterned to have a light-emitting area of 3 mm×3 mm, followed by cleaning. The patterned substrate was disposed in a vacuum chamber. Then, the standard pressure of the chamber was adjusted to 1×10⁻⁶ torr. CuPc (200 Å), NPD (400 Å), BAlq+(btp)₂Ir(acac) (7%) (200 Å), Alq₃ (300 Å), LiF (5 Å) and Al (1000 Å) were sequentially deposited on the ITO glass substrate to manufacture an EL device.

The luminance of the organic EL device was 780 cd/m² at an electric current of 0.9 mA and a voltage of 7.5 V. At this time, the CIE chromaticity coordinates were x=0.659 and y=0.329. The lifetime (defined as the time taken before the luminance of the organic EL device decreases to half its initial value) of the organic EL device was 2,500 hours at 2,000 cd/m².

The organic EL devices fabricated in Examples A-1 to A-5 and Comparative Example A-1 were evaluated for efficiency, CIE chromaticity coordinates, luminance and lifetime characteristics. The results are shown in Table 1.

TABLE 1

| Device | Voltage (V) | Electric current (mA) | Luminance (cd/m²) | Current efficiency (cd/A) | Power efficiency (lm/W) | CIE (X) | CIE (Y) | Life time (h) (half the initial luminance) |
|---|---|---|---|---|---|---|---|---|
| Ex. A-1 | 6.8 | 0.9 | 1,002 | 10.02 | 4.63 | 0.651 | 0.351 | 6,000 |
| Ex. A-2 | 6.5 | 0.9 | 1,034 | 10.34 | 5.00 | 0.650 | 0.350 | 6,000 |
| Ex. A-3 | 6.2 | 0.9 | 908 | 9.08 | 4.60 | 0.655 | 0.352 | 4,500 |
| Ex. A-4 | 6.0 | 0.9 | 940 | 9.40 | 4.28 | 0.653 | 0.351 | 3,500 |
| Ex. A-5 | 7.0 | 0.9 | 955 | 9.55 | 4.28 | 0.656 | 0.353 | 4,000 |
| Comp. Ex. A-1 | 7.5 | 0.9 | 780 | 7.80 | 3.27 | 0.659 | 0.329 | 2,500 |

EXAMPLES B-1 TO B-6 (COMPOUNDS OF FORMULA 2) AND COMPARATIVE EXAMPLE B-1

Example B-1

An ITO-coated glass substrate was patterned to have a light-emitting area of 3 mm×3 mm, followed by cleaning.

After the patterned substrate was disposed in a vacuum chamber, the standard pressure of the chamber was adjusted to $1\times10^{-6}$ torr. CuPc (200 Å), NPD (400 Å), BAlq+A-1 (7%) (200 Å), Alq$_3$ (300 Å), LiF (5 Å) and Al (1000 Å) were sequentially deposited on the ITO glass substrate to fabricate an organic EL device.

The luminance of the organic EL device was 1,020 cd/m$^2$ at an electric current of 0.9 mA and a voltage of 6.3 V. At this time, the CIE chromaticity coordinates were x=0.650 and y=0.361. The lifetime (defined as the time taken before the luminance of the organic EL device decreases to half its initial value) of the organic EL device was 6,000 hours at 2,000 cd/m$^2$.

Example B-2

An ITO-coated glass substrate was patterned to have a light-emitting area of 3 mm×3 mm, followed by cleaning. After the patterned substrate was disposed in a vacuum chamber, the standard pressure of the chamber was adjusted to $1\times10^{-6}$ torr. CuPc (200 Å), NPD (400 Å), BAlq+A-2 (7%) (200 Å), Alq$_3$ (300 Å), LiF (5 Å) and Al (1000 Å) were sequentially deposited on the ITO glass substrate to fabricate an organic EL device.

The luminance of the organic EL device was 989 cd/m$^2$ at an electric current of 0.9 mA and a voltage of 6.2 V. At this time, the CIE chromaticity coordinates were x=0.651 and y=0.362. The lifetime (defined as the time taken before the luminance of the organic EL device decreases to half its initial value) of the organic EL device was 6,000 hours at 2,000 cd/m$^2$.

Example B-3

An ITO-coated glass substrate was patterned to have a light-emitting area of 3 mm×3 mm, followed by cleaning. After the patterned substrate was disposed in a vacuum chamber, the standard pressure of the chamber was adjusted to $1\times10^{-6}$ torr. CuPc (200 Å), NPD (400 Å), BAlq+A-7 (7%) (200 Å), Alq$_3$ (300 Å), LiF (5 Å) and Al (1000 Å) were sequentially deposited on the ITO glass substrate to fabricate an organic EL device.

The luminance of the organic EL device was 866 cd/m$^2$ at an electric current of 0.9 mA and a voltage of 6.1 V. At this time, the CIE chromaticity coordinates were x=0.652 and y=0.361. The lifetime (defined as the time taken before the luminance of the organic EL device decreases to half its initial value) of the organic EL device was 5,000 hours at 2,000 cd/m$^2$.

Example B-4

An ITO-coated glass substrate was patterned to have a light-emitting area of 3 mm×3 mm, followed by cleaning. After the patterned substrate was disposed in a vacuum chamber, the standard pressure of the chamber was adjusted to $1\times10^{-6}$ torr. CuPc (200 Å), NPD (400 Å), BAlq+A-20 (7%) (200 Å), Alq$_3$ (300 Å), LiF (5 Å) and Al (1000 Å) were sequentially deposited on the ITO glass substrate to fabricate an organic EL device.

The luminance of the organic EL device was 843 cd/m$^2$ at an electric current of 0.9 mA and a voltage of 6.2 V. At this time, the CIE chromaticity coordinates were x=0.653 and y=0.363. The lifetime (defined as the time taken before the luminance of the organic EL device decreases to half its initial value) of the organic EL device was 4,000 hours at 2,000 cd/m$^2$.

Example B-5

An ITO-coated glass substrate was patterned to have a light-emitting area of 3 mm×3 mm, followed by cleaning. After the patterned substrate was disposed in a vacuum chamber, the standard pressure of the chamber was adjusted to $1\times10^{-6}$ torr. CuPc (200 Å), NPD (400 Å), BAlq+B-2 (7%) (200 Å), Alq$_3$ (300 Å), LiF (5 Å) and Al (1000 Å) were sequentially deposited on the ITO glass substrate to fabricate an organic EL device.

The luminance of the organic EL device was 883 cd/m$^2$ at an electric current of 0.9 mA and a voltage of 6.2 V. At this time, the CIE chromaticity coordinates were x=0.652 and y=0.361. The lifetime (defined as the time taken before the luminance of the organic EL device decreases to half its initial value) of the organic EL device was 4,000 hours at 2,000 cd/m$^2$.

Example B-6

An ITO-coated glass substrate was patterned to have a light-emitting area of 3 mm×3 mm, followed by cleaning. After the patterned substrate was disposed in a vacuum chamber, the standard pressure of the chamber was adjusted to $1\times10^{-6}$ torr. CuPc (200 Å), NPD (400 Å), BAlq+B-7 (7%) (200 Å), Alq$_3$ (300 Å), LiF (5 Å) and Al (1000 Å) were sequentially deposited on the ITO glass substrate to fabricate an organic EL device.

The luminance of the organic EL device was 896 cd/m$^2$ at an electric current of 0.9 mA and a voltage of 6.0 V. At this time, the CIE chromaticity coordinates were x=0.652 and y=0.362. The lifetime (defined as the time taken before the luminance of the organic EL device decreases to half its initial value) of the organic EL device was 5,000 hours at 2,000 cd/m$^2$.

Comparative Example B-1

An ITO-coated glass substrate was patterned to have a light-emitting area of 3 mm×3 mm, followed by cleaning. After the patterned substrate was disposed in a vacuum chamber, the standard pressure of the chamber was adjusted to $1\times10^{-6}$ torr. CuPc (200 Å), NPD (400 Å), BAlq+(btp)$_2$Ir(acac) (7%) (200 Å), Alq$_3$ (300 Å), LiF (5 Å) and Al (1000 Å) were sequentially deposited on the ITO glass substrate to manufacture an organic EL device.

The luminance of the organic EL device was 780 cd/m$^2$ at an electric current of 0.9 mA and a voltage of 7.5 V. At this time, the CIE chromaticity coordinates were x=0.659 and y=0.329. The lifetime (defined as the time taken before the luminance of the organic EL device decreases to half its initial value) of the organic EL device was 2,500 hours at 2,000 cd/m$^2$.

The organic EL devices fabricated in Examples B-1 to B-6 and Comparative Example B-1 were evaluated for efficiency, CIE chromaticity coordinates, luminance and lifetime characteristics. The results are shown in Table 2.

TABLE 2

| Device | Voltage (V) | Electric current (mA) | Luminance (cd/m$^2$) | Current efficiency (cd/A) | Power efficiency (lm/W) | CIE (X) | CIE (Y) | Life time (h) (half the initial luminance) |
|---|---|---|---|---|---|---|---|---|
| Ex. B-1 | 6.3 | 0.9 | 1,020 | 10.20 | 5.08 | 0.650 | 0.361 | 6,000 |
| Ex. B-2 | 6.2 | 0.9 | 989 | 9.89 | 5.01 | 0.651 | 0.362 | 6,000 |
| Ex. B-3 | 6.0 | 0.9 | 866 | 8.66 | 4.53 | 0.652 | 0.361 | 5,000 |
| Ex. B-4 | 6.2 | 0.9 | 843 | 8.43 | 4.31 | 0.653 | 0.363 | 4,000 |
| Ex. B-5 | 6.1 | 0.9 | 883 | 8.83 | 4.52 | 0.652 | 0.361 | 4,000 |
| Ex. B-6 | 6.0 | 0.9 | 896 | 8.96 | 4.69 | 0.652 | 0.362 | 4,000 |
| Comp. Ex. B-1 | 7.5 | 0.9 | 780 | 7.80 | 3.27 | 0.659 | 0.329 | 2,500 |

EXAMPLES C-1 TO C-6 (COMPOUNDS OF FORMULA 3) AND COMPARATIVE EXAMPLE C-1

Example C-1

An ITO-coated glass substrate was patterned to have a light-emitting area of 3 mm×3 mm, followed by cleaning. After the patterned substrate was disposed in a vacuum chamber, the standard pressure of the chamber was adjusted to 1×10$^{-6}$ torr. CuPc (200 Å), NPD (400 Å), BAlq+A-2 (7%) (200 Å), Alq$_3$ (300 Å), LiF (5 Å) and Al (1000 Å) were sequentially deposited on the ITO glass substrate to fabricate an organic EL device.

The luminance of the organic EL device was 1,328 cd/m$^2$ at an electric current of 0.9 mA and a voltage of 5.8 V. At this time, the CIE chromaticity coordinates were x=0.654 and y=0.339. The lifetime (defined as the time taken before the luminance of the organic EL device decreases to half its initial value) of the organic EL device was 3,900 hours at 2,000 cd/m$^2$.

Example C-2

An ITO-coated glass substrate was patterned to have a light-emitting area of 3 mm×3 mm, followed by cleaning. After the patterned substrate was disposed in a vacuum chamber, the standard pressure of the chamber was adjusted to 1×10$^{-6}$ torr. CuPc (200 Å), NPD (400 Å), BAlq+A-3 (7%) (200 Å), Alq$_3$ (300 Å), LiF (5 Å) and Al (1000 Å) were sequentially deposited on the ITO glass substrate to fabricate an organic EL device.

The luminance of the organic EL device was 1,430 cd/m$^2$ at an electric current of 0.9 mA and a voltage of 5.9 V. At this time, the CIE chromaticity coordinates were x=0.648 and y=0.342. The lifetime (defined as the time taken before the luminance of the organic EL device decreases to half its initial value) of the organic EL device was 4,000 hours at 2,000 cd/m$^2$.

Example C-3

An ITO-coated glass substrate was patterned to have a light-emitting area of 3 mm×3 mm, followed by cleaning. After the patterned substrate was disposed in a vacuum chamber, the standard pressure of the chamber was adjusted to 1×10$^{-6}$ torr. CuPc (200 Å), NPD (400 Å), BAlq+A-6 (7%) (200 Å), Alq$_3$ (300 Å), LiF (5 Å) and Al (1000 Å) were sequentially deposited on the ITO glass substrate to fabricate an organic EL device.

The luminance of the organic EL device was 1,411 cd/m$^2$ at an electric current of 0.9 mA and a voltage of 6.2 V. At this time, the CIE chromaticity coordinates were x=0.657 and y=0.337. The lifetime (defined as the time taken before the luminance of the organic EL device decreases to half its initial value) of the organic EL device was 4,200 hours at 2,000 cd/m$^2$.

Example C-4

An ITO-coated glass substrate was patterned to have a light-emitting area of 3 mm×3 mm, followed by cleaning. After the patterned substrate was disposed in a vacuum chamber, the standard pressure of the chamber was adjusted to 1×10$^{-6}$ torr. CuPc (200 Å), NPD (400 Å), BAlq+A-7 (7%) (200 Å), Alq$_3$ (300 Å), LiF (5 Å) and Al (1000 Å) were sequentially deposited on the ITO glass substrate to fabricate an organic EL device.

The luminance of the organic EL device was 1,320 cd/m$^2$ at an electric current of 0.9 mA and a voltage of 6.1 V. At this time, the CIE chromaticity coordinates were x=0.659 and y=0.327. The lifetime (defined as the time taken before the luminance of the organic EL device decreases to half its initial value) of the organic EL device was 4,000 hours at 2,000 cd/m$^2$.

Example C-5

An ITO-coated glass substrate was patterned to have a light-emitting area of 3 mm×3 mm, followed by cleaning. After the patterned substrate was disposed in a vacuum chamber, the standard pressure of the chamber was adjusted to 1×10$^{-6}$ torr. CuPc (200 Å), NPD (400 Å), BAlq+A-16 (7%) (200 Å), Alq$_3$ (300 Å), LiF (5 Å) and Al (1000 Å) were sequentially deposited on the ITO glass substrate to fabricate an organic EL device.

The luminance of the organic EL device was 1,361 cd/m$^2$ at an electric current of 0.9 mA and a voltage of 6.3 V. At this time, the CIE chromaticity coordinates were x=0.641 and y=0.341. The lifetime (defined as the time taken before the luminance of the organic EL device decreases to half its initial value) of the organic EL device was 3,700 hours at 2,000 cd/m$^2$.

Example C-6

An ITO-coated glass substrate was patterned to have a light-emitting area of 3 mm×3 mm, followed by cleaning. After the patterned substrate was disposed in a vacuum chamber, the standard pressure of the chamber was adjusted to 1×10$^{-6}$ torr. CuPc (200 Å), NPD (400 Å), BAlq+A-17 (7%) (200 Å), Alq$_3$ (300 Å), LiF (5 Å) and Al (1000 Å) were sequentially deposited on the ITO glass substrate to fabricate an organic EL device.

The luminance of the organic EL device was 1,431 cd/m$^2$ at an electric current of 0.9 mA and a voltage of 6.6 V. At this time, the CIE chromaticity coordinates were x=0.652 and y=0.342. The lifetime (defined as the time taken before the luminance of the organic EL device decreases to half its initial value) of the organic EL device was 3,500 hours at 2,000 cd/m².

Comparative Example C-1

An ITO-coated glass substrate was patterned to have a light-emitting area of 3 m×3 mm, followed by cleaning. After the patterned substrate was disposed in a vacuum chamber, the standard pressure of the chamber was adjusted to $1\times10^{-6}$ torr. CuPc (200 Å), NPD (400 Å), BAlq+(btp)₂Ir(acac) (7%) (200 Å), $Alq_3$ (300 Å), LiF (5 Å) and Al (1000 Å) were sequentially deposited on the ITO glass substrate to manufacture an organic EL device.

The luminance of the organic EL device was 780 cd/m² at an electric current of 0.9 mA and a voltage of 7.5 V. At this time, the CIE chromaticity coordinates were x=0.659 and y=0.329. The lifetime (defined as the time taken before the luminance of the organic EL device decreases to half its initial value) of the organic EL device was 2,500 hours at 2,000 cd/m².

The organic EL devices fabricated in Examples C-1 to C-6 and Comparative Example C-1 were evaluated for efficiency, CIE chromaticity coordinates, luminance and lifetime characteristics. The results are shown in Table 3.

TABLE 3

| Device | Voltage (V) | Electric current (mA) | Luminance (cd/m²) | Current efficiency (cd/A) | Power efficiency (lm/W) | CIE (X) | CIE (Y) | Life time (h) (half the initial luminance) |
|---|---|---|---|---|---|---|---|---|
| Ex. C-1 | 5.8 | 0.9 | 1,328 | 13.28 | 7.19 | 0.654 | 0.339 | 3,900 |
| Ex. C-2 | 5.9 | 0.9 | 1,430 | 14.30 | 7.61 | 0.648 | 0.342 | 4,000 |
| Ex. C-3 | 6.2 | 0.9 | 1,411 | 14.11 | 7.15 | 0.657 | 0.337 | 4,200 |
| Ex. C-4 | 6.1 | 0.9 | 1,320 | 13.20 | 6.79 | 0.659 | 0.327 | 4,000 |
| Ex. C-5 | 6.3 | 0.9 | 1,361 | 13.61 | 6.78 | 0.641 | 0.341 | 3,700 |
| Ex. C-6 | 6.6 | 0.9 | 1,431 | 14.31 | 6.81 | 0.644 | 0.337 | 3,500 |
| Comp. Ex. C-1 | 7.5 | 0.9 | 780 | 7.8 | 3.3 | 0.659 | 0.329 | 2,500 |

EXAMPLES D-1 TO D-5 (COMPOUNDS OF FORMULA 4) AND COMPARATIVE EXAMPLE D-1

Example D-1

An ITO-coated glass substrate was patterned to have a light-emitting area of 3 mm×3 mm, followed by cleaning. After the patterned substrate was disposed in a vacuum chamber, the standard pressure of the chamber was adjusted to $1\times10^{-6}$ torr. CuPc (200 Å), NPD (400 Å), BAlq+A-2 (7%) (200 Å), $Alq_3$ (300 Å), LiF (5 Å) and Al (1000 Å) were sequentially deposited on the ITO glass substrate to fabricate an organic EL device.

The luminance of the organic EL device was 1,401 cd/m² at an electric current of 0.9 mA and a voltage of 5.7 V. At this time, the CIE chromaticity coordinates were x=0.651 and y=0.341. The lifetime (defined as the time taken before the luminance of the organic EL device decreases to half its initial value) of the organic EL device was 4,000 hours at 2,000 cd/m².

Example D-2

An ITO-coated glass substrate was patterned to have a light-emitting area of 3 mm×3 mm, followed by cleaning. After the patterned substrate was disposed in a vacuum chamber, the standard pressure of the chamber was adjusted to $1\times10^{-6}$ torr. CuPc (200 Å), NPD (400 Å), BAlq+A-3 (7%) (200 Å), $Alq_3$ (300 Å), LiF (5 Å) and Al (1000 Å) were sequentially deposited on the ITO glass substrate to fabricate an organic EL device.

The luminance of the organic EL device was 1,375 cd/m² at an electric current of 0.9 mA and a voltage of 6.1 V. At this time, the CIE chromaticity coordinates were x=0.649 and y=0.337. The lifetime (defined as the time taken before the luminance of the organic EL device decreases to half its initial value) of the organic EL device was 4,500 hours at 2,000 cd/m².

Example D-3

An ITO-coated glass substrate was patterned to have a light-emitting area of 3 mm×3 mm, followed by cleaning. After the patterned substrate was disposed in a vacuum chamber, the standard pressure of the chamber was adjusted to $1\times10^{-6}$ torr. CuPc (200 Å), NPD (400 Å), BAlq+A-6 (7%) (200 Å), $Alq_3$ (300 Å), LiF (5 Å) and Al (1000 Å) were sequentially deposited on the ITO glass substrate to fabricate an organic EL device.

The luminance of the organic EL device was 1,320 cd/m² at an electric current of 0.9 mA and a voltage of 6.3 V. At this time, the CIE chromaticity coordinates were x=0.648 and y=0.338. The lifetime (defined as the time taken before the luminance of the organic EL device decreases to half its initial value) of the organic EL device was 4,400 hours at 2,000 cd/m².

Example D-4

An ITO-coated glass substrate was patterned to have a light-emitting area of 3 mm×3 mm, followed by cleaning. After the patterned substrate was disposed in a vacuum chamber, the standard pressure of the chamber was adjusted to $1\times10^{-6}$ torr. CuPc (200 Å), NPD (400 Å), BAlq+A-19 (7%) (200 Å), $Alq_3$ (300 Å), LiF (5 Å) and Al (1000 Å) were sequentially deposited on the ITO glass substrate to fabricate an organic EL device.

The luminance of the organic EL device was 1,268 cd/m² at an electric current of 0.9 mA and a voltage of 6.1 V. At this time, the CIE chromaticity coordinates were x=0.650 and y=0.340. The lifetime (defined as the time taken before the luminance of the organic EL device decreases to half its initial value) of the organic EL device was 3,600 hours at 2,000 cd/m².

Example D-5

An ITO-coated glass substrate was patterned to have a light-emitting area of 3 mm×3 mm, followed by cleaning.

After the patterned substrate was disposed in a vacuum chamber, the standard pressure of the chamber was adjusted to $1\times10^{-6}$ torr. CuPc (200 Å), NPD (400 Å), BAlq+B-2 (7%) (200 Å), Alq$_3$ (300 Å), LiF (5 Å) and Al (1000 Å) were sequentially deposited on the ITO glass substrate to fabricate an organic EL device.

The luminance of the organic EL device was 1,257 cd/m$^2$ at an electric current of 0.9 mA and a voltage of 5.9 V. At this time, the CIE chromaticity coordinates were x=0.639 and y=0.340. The lifetime (defined as the time taken before the luminance of the organic EL device decreases to half its initial value) of the organic EL device was 4,000 hours at 2,000 cd/m$^2$.

Comparative Example D-1

An ITO-coated glass substrate was patterned to have a light-emitting area of 3 mm×3 mm, followed by cleaning. After the patterned substrate was disposed in a vacuum chamber, the standard pressure of the chamber was adjusted to $1\times10^{-6}$ torr. CuPc (200 Å), NPD (400 Å), BAlq+(btp)$_2$Ir (acac) (7%) (200 Å), Alq$_3$ (300 Å), LiF (5 Å) and Al (1000 Å) were sequentially deposited on the ITO glass substrate to manufacture an organic EL device.

The luminance of the organic EL device was 780 cd/m$^2$ at an electric current of 0.9 mA and a voltage of 7.5 V. At this time, the CIE chromaticity coordinates were x=0.659 and y=0.329. The lifetime (defined as the time taken before the luminance of the organic EL device decreases to half its initial value) of the organic EL device was 2,500 hours at 2,000 cd/m$^2$.

The organic EL devices fabricated in Examples D-1 to D-5 and Comparative Example D-1 were evaluated for efficiency, CIE chromaticity coordinates, luminance and lifetime characteristics. The results are shown in Table 4.

TABLE 4

| Device | Voltage (V) | Electric current (mA) | Luminance (cd/m$^2$) | Current efficiency (cd/A) | Power efficiency (lm/W) | CIE (X) | CIE (Y) | Life time (h) (half the initial luminance) |
|---|---|---|---|---|---|---|---|---|
| Ex. D-1 | 5.7 | 0.9 | 1,401 | 14.01 | 7.72 | 0.651 | 0.341 | 4,000 |
| Ex. D-2 | 6.1 | 0.9 | 1,375 | 13.75 | 7.08 | 0.649 | 0.361 | 4,000 |
| Ex. D-3 | 6.3 | 0.9 | 1,320 | 13.20 | 6.58 | 0.648 | 0.338 | 4,400 |
| Ex. D-4 | 6.1 | 0.9 | 1,268 | 12.68 | 6.53 | 0.650 | 0.340 | 3,600 |
| Ex. D-5 | 5.9 | 0.9 | 1,257 | 12.57 | 6.69 | 0.639 | 0.340 | 4,000 |
| Comp Ex. D-1 | 7.5 | 0.9 | 780 | 7.8 | 3.3 | 0.659 | 0.329 | 2,500 |

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. An organic electroluminescent (EL) device comprising
an anode,
a hole injecting layer,
a hole transport layer,
a light-emitting layer comprising a dopant,
an electron transport layer,
an electron injecting layer, and
a cathode
laminated in this order,
wherein the dopant is a red phosphorescent compound and is present in an amount of 0.5 to 20% by weight, based on the weight of a host, and
wherein the host is BAlq and the red phosphorescent compound is of Formula 1 below:

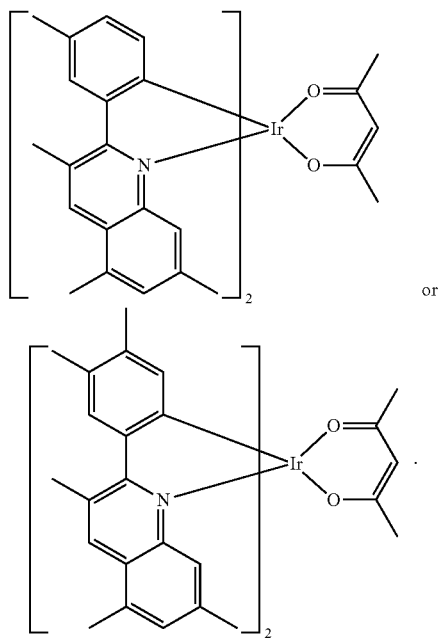

or

2. An organic electroluminescent (EL) device comprising
an anode,
a hole injecting layer,
a hole transport layer,
a light-emitting layer comprising a dopant,
an electron transport layer,
an electron injecting layer, and
a cathode
laminated in this order,
wherein the dopant is a red phosphorescent compound and is present in an amount of 0.5 to 20% by weight, based on the weight of a host, and
wherein the host is BAlq and the red phosphorescent compound is of Formula 2 below:

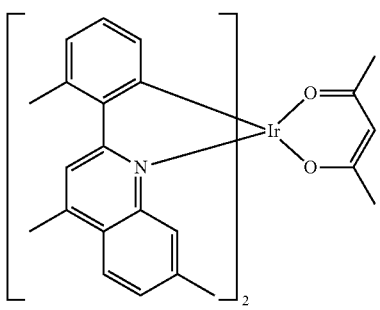

or

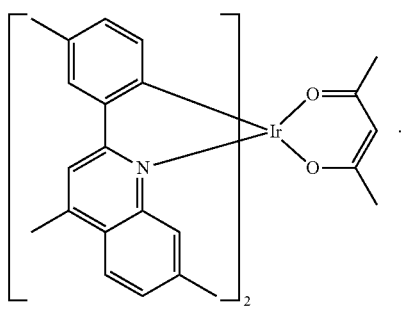

3. An organic electroluminescent (EL) device comprising
an anode,
a hole injecting layer,
a hole transport layer,
a light-emitting layer comprising a dopant,
an electron transport layer,
an electron injecting layer, and
a cathode
laminated in this order,
   wherein the dopant is a red phosphorescent compound and is present in an amount of 0.5 to 20% by weight, based on the weight of a host, and
   wherein the host is BAlq and the red phosphorescent compound is of Formula 3 below:

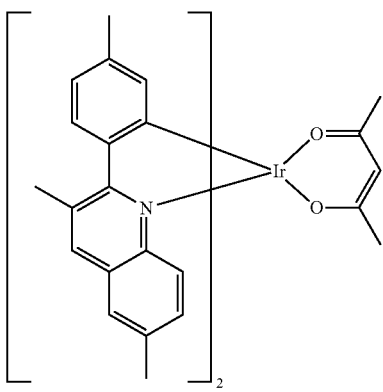

or

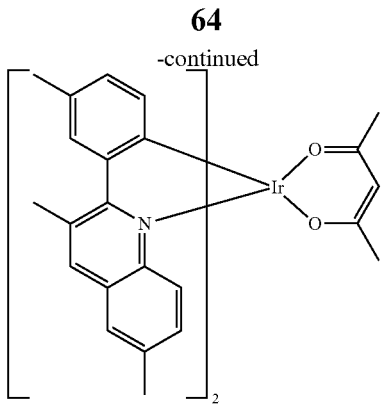

4. An organic electroluminescent (EL) device comprising
an anode,
a hole injecting layer,
a hole transport layer,
a light-emitting layer comprising a dopant,
an electron transport layer,
an electron injecting layer, and
a cathode
laminated in this order,
   wherein the dopant is a red phosphorescent compound and is present in an amount of 0.5 to 20% by weight, based on the weight of a host, and
   wherein the host is BAlq and the red phosphorescent compound selected from Formula 4 below:

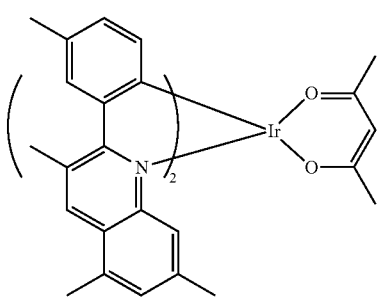

,

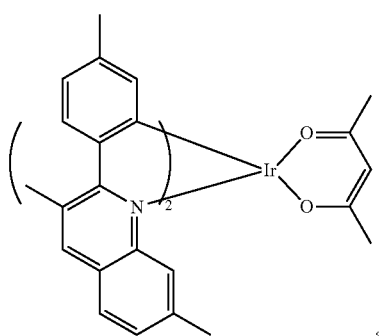

and

-continued
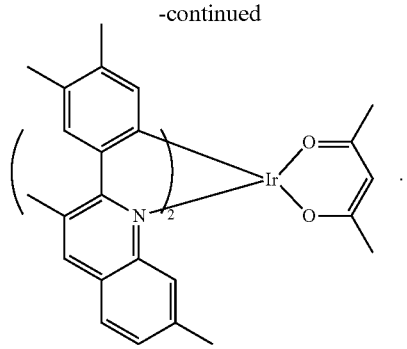
* * * * *